US007169567B1

(12) United States Patent
Gardella et al.

(10) Patent No.: US 7,169,567 B1
(45) Date of Patent: Jan. 30, 2007

(54) SCREENING ASSAY UTILIZING THE PTH RECEPTOR

(75) Inventors: Thomas J. Gardella, Needham, MA (US); Henry M. Kronenberg, Belmont, MA (US); John T. Potts, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/869,565

(22) PCT Filed: Dec. 31, 1998

(86) PCT No.: PCT/US98/27862

§ 371 (c)(1),
(2), (4) Date: Oct. 17, 2001

(87) PCT Pub. No.: WO00/40698

PCT Pub. Date: Jul. 13, 2000

(51) Int. Cl.
G01N 33/567 (2006.01)
C12N 5/06 (2006.01)
C12N 15/63 (2006.01)
C07K 14/72 (2006.01)
C07H 21/04 (2006.01)

(52) U.S. Cl. ............ 435/7.21; 435/325; 435/455; 530/350; 536/23.5

(58) Field of Classification Search ........... 436/501; 435/7.1; 530/350; 514/2
See application file for complete search history.

(56) References Cited

U.S. PATENT DOCUMENTS

| 4,086,196 | A |   | 4/1978  | Tregear |
|-----------|---|---|---------|---------|
| 5,217,896 | A |   | 6/1993  | Kramer et al. |
| 5,494,806 | A | * | 2/1996  | Segre et al. ............ 435/69.1 |
| 6,417,333 | B1 |  | 7/2002  | Bringhurst et al. |
| 6,495,662 | B1 | * | 12/2002 | Gardella et al. ........... 530/300 |
| 6,537,965 | B1 |  | 3/2003  | Bringhurst et al. |
| 6,541,220 | B1 |  | 4/2003  | Jüppner et al. |
| 6,803,213 | B1 |  | 10/2004 | Bringhurst et al. |
| 2003/0144209 | A1 |  | 7/2003 | Bringhurst et al. |
| 2003/0162256 | A1 |  | 8/2003 | Juppner et al. |
| 2003/0166838 | A1 |  | 9/2003 | Gardella et al. |
| 2005/0026839 | A1 |  | 2/2005 | Gardella |

FOREIGN PATENT DOCUMENTS

| CA | 2126132 | 12/1995 |
|----|---------|---------|
| CA | 2126299 | 12/1995 |
| EP | 0 464 533 | 1/1992 |
| EP | 0 477 885 | 4/1992 |
| EP | 0 561 412 | 9/1993 |
| EP | 0 748 817 | 12/1996 |
| GB | 2 269 176 | 2/1994 |
| WO | WO 87/01130 | 2/1987 |
| WO | WO 91/05050 | 4/1991 |
| WO | WO 92/01810 | 2/1992 |
| WO | WO 92/17602 | 10/1992 |
| WO | WO 95/11988 | 5/1995 |
| WO | WO 97/02834 | 1/1997 |
| WO | WO 98/05683 | 2/1998 |
| WO | WO 99/18945 | 4/1999 |
| WO | WO 00/31137 | 6/2000 |
| WO | WO 00/32775 | 6/2000 |
| WO | WO 00/39278 | 7/2000 |
| WO | WO 01/23427 | 4/2001 |
| WO | WO 01/23521 | 4/2001 |
| WO | WO 00/23594 | 8/2001 |
| WO | WO 00/31266 | 9/2001 |
| WO | WO 00/40698 | 10/2001 |
| WO | WO 03/009804 | 2/2003 |
| WO | WO 2004/067021 | 8/2004 |
| WO | WO 2004/093902 | 11/2004 |
| WO | WO 2005/009358 | 2/2005 |

OTHER PUBLICATIONS

Chorev et al. (1991) Biochemistry 30(24): 5968-5974.*
Goud et al. (1991) J Bone Miner Res 6(8): 781-789.*
Horiuchi et al. (1987) Am J Physiol 253: E187-192.*
Lee et al. (1995) Mol Endocrinol 9(10): 1269-1278.*
Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trend in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Sunyaev et al. 2004. Proteins: Structure, Function and Bioinformatics. 54: 569-582.*
Vogt et al. 1995. J Mol Biol. 249: 816-831.*
Abou-Samra, A.B., et al., "Phorbol 12-Myristate 13-Acetate and Vasopressin Potentiate the Effect of Corticotropin-releasing Factor on Cyclic AMP Production in Rat Anterior Pituitary Cells," *J. Biol. Chem.* 262:1129-1136, The American Society for Biochemistry and Molecular Biology, Inc. (1987).
Abou-Samra, A.B., et al., "Cyclic Andenosine 3', 5' - Monophosphate (cAMP)—Dependent and cAMP-Independent Regulation of Parathyroid Hormoe Receptors on UMR 106-01 Osteoblastic Osteosarcoma Cells," *Endocrinology* 129:2547-2554, The Endocrine Society (1991).

(Continued)

*Primary Examiner*—Gary B. Nickol
*Assistant Examiner*—Zachary C. Howard
(74) *Attorney, Agent, or Firm*—Sterne, Kessler, Goldstein & Fox P.L.L.C.

(57) ABSTRACT

The invention provides a novel PTH receptor polypeptide, rΔNt, characterized by a deletion of the extracellular amino-terminus, ligand binding domain of the receptor. Additionally disclosed are nucleic acid molecules encoding the receptor. The receptor has a minimal domain for ligand binding and is useful in screening assays designed for the identification of agonists and antagonists of PTH receptor activity.

10 Claims, 8 Drawing Sheets

OTHER PUBLICATIONS

Abou-Samra, A.B., et al., "Non-Homologous Sequences of Parathyroid and the Parathyroid Hormone Relateed Peptied Bind to a Common Recceptor on ROS 17/2.8 Cells," *Endocrinology* 125:2215-2217, The Endocrine Society (1989).

Azarani, A., et al., "Structurally Diverse N-terminal Peptides of Parathyroid Hormone (PTH) and PTH-related Peptide (PTHRP) Inhibit the $NA^+/H^+$ Exchanger NHE3 Isoform by Binding to the PTH/PTHRP Receptor Type I and Activating Distinct Signaling Pathways, " *J. Biol. Chem.* 271:14931-14936, The American Society for Biochemistry and Molecular Biology, Inc. (1996).

Barbier, J.-R., et al., "Bioactivities and Secondary Structures of Constrained Analogues of Human Parathyroid Hormone: Cyclic Lactams of the Receptor Binding Region," *J. Med. Chem.* 40:1373-1380, Americna Chemical Society (Apr. 1997).

Bennett, D., et al., "Kinetic Characterization of the Interaction of Biotinylated Human Interleukin 5 with an Fc Chimera of its Receptor α Subunit and Development of a ELISA Screening Assay using Real-Time Interaction Biosensor Analysis, " *J. Molec. Recognition* 8:52-58, John Wiley & Sons, Ltd. (1995).

Bergwitz, C., et al., "Full Activation of Chimeric Receptors by Hybrids between Parathyroid Hormone and Calcitonin," *J. Biol. Chem.* 271:26469-26472, The American Society for Biochemistry and Molecular Biology, Inc. (1996).

Bergwitz, C., et al., "Residues in the Membrane-spanning and Extracellular Loop Regions of the Parathyroid Hormone (PTH)-2 Receptor Determine Signaling Selecivity for PTH and PTH-related Peptide," *J. Biol. Chem.* 272:28861-28868, The American Society for Biochemistry and Molecular Biology, Inc. (Nov. 1997).

Bisello, A., et al., "Parathyroid Hormone-Receptor Interactions Identified Directly by Photocross-linking and Molecular Modeling Studies," *J. Biol. Chem.* 273:22498-22505, The American Society for Biochemistry and Molecular Biology, Inc. (Aug. 1998).

Bowie, J.U., et al., "Deciphering the Message in Protein Seuences: Tolerance to Amino Acid Substitutions," *Science* 247:1306-1310, American Association for the Advancement of Science (1990).

Caulfield, M.P., et al., "The Bovine Renal Parathyroid Hormone (PTH) Receptor Has Equal Affinity for Two Different Amino Acid Sequences: The Receptor Binding Domains of the PTH and PTH-Related Protein Are Located within the 14-34 Region" *Endocrinology* 127:83-87, The Endocrine Society (1990).

Chorev, M., et al., "Modifications of Position 12 in Parathyroid Hormone and Parathyroid Hormone Related Protein: Thyroid the Design of Highly Potent Antagonists," *Biochem.* 29:1580-1586, American Chemical Society (1990).

Cleland, J.L., et al., "The Development of Stable Protein Formulations: A Close Look at Protein Aggregation, Deamidation, and Oxidation," *Crit. Rev. Ther. Drug Carrier Systems* 10:307-377, CRC Press, Inc. (1993).

Cohen, F.E., et al., "Analogues of Parathyroid Hormone Modified at Positions 3 and 6. Effects on Receptor Binding and Activation of Adenylyl Cyclase in Kidney and Bone," *J. Biol. Chem.* 266:1997-2004, The American Society for Biochemistry and Molecular Biology, Inc. (1991).

Cunningham, B.C., and Wells, J.A., "High-Resolution Epitope Mapping of hGH-Receptor Interactions by Alanine-Scanning Mutagenesis," *Science* 244:1081-1085, American Association for the Advancement of Science (1989).

Dautzenberg, F., et al., "Mapping of the ligand-selective domain of the *Xenopus laevis* corticotropin-releasing factor receptor 1: Implications for the ligand-binding site," *Proc. Natl. Acad. Sci. USA* 95:4941-4946, National Academy of Sciences (Apr. 1998).

de Vos, A.M., et al., "Human Growth Hormone and Extracellular Domain of Its Receptor: Crystal Structure of the Complex," *Science* 255:306-312, American Association for the Advancement of Science (1992).

DeAlmeida, V., and Mayo, K., "Identification of Binding Domains of the Growth Hormone-Releasing Hormone Receptor by Analysis of Mutant and Chimeric Receptor Proteins," *Mol. Endocrinol.* 12:750-765, The Endocrine Society (May 1998).

Dempster, D.W., et al., "Anabolic Actions of Parathyroid Hormone on Bone," *Endocr. Rev.* 14:690-709, The Endocrine Society (1993).

Donahue, H.J., et al., "Differential Effects of Parathyroid Hormone and Its Analogues on Cytosolic Calcium Ion and cAMP Levels in Cultured Rat Osteoblast-like Cells," *J. Biol. Chem.* 263:13522-13527, The American Society for Biochemistry and Molecular Biology, Inc. (1988).

Gardella, T.J., et al., "Mutational Analysis of the Receptor-activating Region of Human Parathyroid Hormone," *J. Biol. Chem.* 266:13141-13146, The American Society for Biochemistry and Molecular Biology, Inc. (1991).

Gardella, T.J., et al., "Determinants of [$Arg^2$] PHT-(1-34) Binding and Signaling in the Transmembrane Region of the Parathyroid Hormone Receptor," *Endocrinology* 135:1186-1194, The Endocrine Society (1994).

Gardella, T.J., et al., "Analysis of Parathyroid Hormone's Principal Receptor-Binding Region by Site-Directed Mutagenesis and Analog Design," *Endocrinology* 132:2024-2030, The Endocrine Society (1993).

Gardella, T.J., et al., "Transmembrane Residues of the Parathyroid Hormone (PTH) /PTH-related Peptide Receptor That Specifically Affect Binding and Signaling by Agonist Ligands," *J. Biol. Chem.* 271:12820-12825, The American Society for Biochemistry and Molecular Biology, Inc. (1996).

Gardella, T.J., et al., "Parathyroid Hormone (PTH)-PTH-related Peptide Hybrid Peptides Reveal Functional Interactions between the 1-14 and 15-34 Domains of the Ligand," *J. Biol. Chem.* 270:6584-6588, The American Society for Biochemistry and Molecular Biology, Inc. (1995).

Gentz, R., et al., "Bioassay for trans-activation using purified human immunodeficiency virus *tat*-encoded protein: Trans-activated requires mRNA synthesis," *Proc. Natl. Acad. Sci. USA* 86:821-824, National Academy of Sciences (1989).

Gombert, F., et al., "Alanine and D-Amino Acid Scan of Human Parathyroid Hormone," in *Peptides: Chemistry, Structure and Biology. Proceedings of the 14th American Peptide Symposium*, Jun. 18-23 , Kaumaya, P.T.P., and Hodges, R.S., eds., Mayflower Scientific Ltd., Kingswinford, UK, pp. 661-662 (1996).

Guo, J., et al., "Parathyroid Hormone (PTH)/PTH-Related Peptide Receptor Density Modulates Activation of Phospholipase C and Phosphate Transport by PTH in LLC-PK1 Cells," *Endocrinology* 136:3884-3891, The Endocrine Society (1995).

Hjorth, S., et al., "Constitutive Activity of Glucagon Receptor Mutants," *Mol. Endocrinol.* 12:78-86, The Endocrine Society (Jan. 1998).

Holtmann, M., et al., "Critical Contributions of Amino-terminal Extracellular Domains in Agonist Binding and Activation of Secretin and Vasoactive Intestinal Polypeptide Receptors. Studies of Chimeric Receptors," *J. Biol. Chem.* 270:14394-14398, The American Society for Biochemistry and Molecular Biology, Inc. (1995).

Horiuchi, N., et al., "A Parathyroid Hormone Inhibitor in vivo: Design and Biological Evaluation of a Hormone Analog," *Science* 220:1053-1055, American Association for the Adancement of Science (1983).

Hruska, K.A., et al., "Stimulation of Inositol Trisphosphate and Diacylglycerol Production in Renal Tubular Cells by Parathyroid Hormone," *J. Clin. Invest.* 79:230-239, The Rockefeller University Press (1987).

Ji, I.H., and Ji, T.H., "Human Choriogonadotropin Binds to a Lutropin Receptor with Essentially No N-terminal Extension and Stimulates cAMP Synthesis," *J. Biol. Chem.* 266:13076-13079, The American Society for Biochemistry and Molecular Biology, Inc. (1991).

Johanson, K., et al., "Binding Interactions of Human Interleukin 5 with Its Receptor α Subunit. Large Scale Production, Structural, and Functional Studies of Drosophila-Expressed Recombinant Proteins," *J. Biol. Chem.* 270:9459-9471, The American Society for Biochemistry and Molecular Biology, Inc. (1995).

Jüppner, H., et al., "A G Protein-Linked Receptor for Parathyroid Hormone and Parathyroid Hormone-Related Peptide," *Science* 254:1024-1026, American Association for the Advancement of Science (1991).

Jüppner, H., et al., "The Extracellular Animo-Terminal Region of the Parathyroid Hormone (PTH)/PTH-Related Peptide Receptor Determines the Binding Affinity for Carboxyl-Terminal Fragments of PTH-(1-34)," *Endocrinology* 134:879-884, The Endocrine Society (1994).

Kolakowski, L.F., "GCRDb: A G-Protein-Coupled Receptor Database," *Receptors and Channels* 2:1-7, Hardwood Academic Publishers (1994).

Kronenberg, H.M., et al., "Parathyroid Hormone: Biosynthesis, Secretion, Chemistry, and Action," in *Handbook of Experimental Pharmacology*, vol. 107, Mundy, G.R., and Martin, T.J., eds., Springer-Verlag, Berlin, Germany, pp. 507-567 (1993).

Lanske, B., et al., "PTH/PTHrP Receptor in Early Development and Indian Hedgehog-Regulated Bone Growth," Science 273:663-666, American Association for the Advancement of Science (1996).

Lee, C., et al., "Homolog-Scanning Mutagenesis of the Parathyroid Hormone (PTH) Receptor Reveals PTH-(1-34) Binding Determinants in the Third Extracellular Loop," *Mol. Endocrinol.* 9:1269-1278, The Endocrine Society (1995).

Lee, C., et al., "Role of the Extacellular Regions of the Parathyroid Hormone (PTH)/PTH-Related Peptide Receptor in Hormone Binding," *Endocrinology* 135:1488-1495, The Endocrine Society (1994).

Luck, M.D., et al., "The (1-14) Fragment of Parathyroid Hormone (PTH) Activates Intact and Amino-Terminally Truncated PTH-1 Receptors," *Mol. Endocrinol.* 13:670-680, The Endocrine Society (May 1999).

Mannstadt, M., et al., "Evidence for a Ligand Interaction Site at the Amino-Terminus of the Parathyroid Hormone (PTH)/PTH-related Protein Receptor from Cross-linking and Mutational Studies," *J. Biol. Chem.* 273:16890-16896, The American Society for Biochemistry and Molecular Biology, Inc. (Jul. 1998).

McCuaig, K.A., et al., "Molecular cloning of the gene encoding the mouse parathyroid hormone/parathyroid hormone-related peptide receptor," *Proc. Natl. Acad. Sci. USA* 91:5051-5055, National Academy of Sciences (1994).

McGeoch, D.J., "On the predictive recognition of signal peptide sequences," *Virus Res.* 3:271-286, Elsevier Science B.V. (1985).

Mikayama, T., et al., "Molecular cloning and functional expression of a cDNA encoding glycosylation-inhibiting factor," *Proc. Natl. Acad. Sci USA* 90:10056-10060, National Academy of Sciences (1993).

Nakai, K., and Kanehisa, M., "A Knowledge Base for Predicting Protein Localization Sites in Eukaryotic Cells," *Genomics* 14:897-911, Academic Press, Inc. (1992).

Neugebauer, W., et al., "Solution Structure and Adenylyl Cyclase Stimulating Activities of C-Terminal Truncated Human Parathyroid Hormone Analogues," *Biochem.* 34:8835-8842, American Chemical Society (1995).

Nielsen, H., et al., *Prot. Eng.* 10:1-6, Identification of prokaryotic and eukaryotic signal peptides and prediction of their cleavage sites, Oxford university Press (Jan. 1997).

Nussbaum, S.R., et al., "Parathyroid Hormone•Renal Receptor Interactions. Demonstration of Two Receptor-Binding Domains," *J.Biol.Chem.* 255:10183-10187, The American Society of Biological Chemists, Inc. (1980).

Nutt, R.F., et al., "Removal of Partial Agonism From Parathyroid Hormone (PTH)-Related Protein-(7-34) $NH_2$ by Substitution of PTH Amino Acids at Positions 10 and 11," *Endocrinology* 127:491-493, The Endocrine Society (1990).

Pinckard, R.N., et al., "Factors Influencing the Immune Response. I. Effects of the Physical State of the Antigen and of Lymphoreticular Cell Proliferation on the Response to Intravenous Injection of Bovine Serum Albumin in Rabbits," *Clin. Exp. Immunol.* 2:331-340, Blackwell Scientific Publications (1967).

Rieger, R., et al., "allele" in *Glossary of Genetics and Cytogenetics. Classic and Molecular. Fourth Completely Revised Edition*, Springer-Verlag, Berlin, Germany, pp. 17-18 (1976).

Rixon, R.H., et al., "Parathyroid Hormone Fragments May Stimulate Bone Growth in Ovariectomized Rats by Activating Adenylyl Cyclase," *J. Bone Min. Res.* 9:1179-1189, Mary Ann Liebert, Inc. (1994).

Robbins, D.C., et al., "Antibodies to Covalent Aggregates of Insulin in Blood of Insulin-using Diabetic Patients," *Diabetes* 36:838-841, American Diabetes Association (1987).

Rubin, D.A., and Jüppner, H., "Zebrafish Express the Common Parathyroid Hormone/Parathyroid Hormone-related Peptide Receptor (PTH1R) and a Novel Receptor (PTH3R) That Is Preferentially Activated by Mammalian and Fugufish Parathyroid Hormone-related Peptide," *J. Biol. Chem.* 274:28185-28190, The American Society for Biochemistry and Molecular Biology, Inc. (Oct. 1999).

Rosenblatt, M., "Parathyroid Hormone: Chemistry and Structure-Activity Relations," in *Pathobiology Annual vol. 11*, Ioachim, H.L., ed., Raven Press, Ny, pp. 53-86 (1981).

Shimizu, M., et al., "Type-Substitution Analysis of the Amino-Terminal Fragment of Parathyroid Hormone, PTH(1-14): An Approach toward New Low Molecular Weight PTH Agonists," *J. Bone Min. Res.* 14 (*suppl. 1*):Abs. No. F398, Mary Ann Liebert, Inc. (Sep. 1999).

Shimizu, M., et al., "Autoactivation of Type-1 Parathyroid Hormone Receptors Containing a Tethered Ligand," *J. Biol. Chem.* 275:19456-19460, The American Society for Biochemistry and Molecular Biology, Inc. (Jun. 2000).

Shimizu, M., et al., "Minimization of Parathyroid Hormone. Novel Amino-Terminal Parathyroid Hormone Fragments with Enhanced Potency in Activating the Type-1 Parathyroid Hormone Receptor," *J. Biol. Chem.* 275:21836-21843, The American Society for Biochemistry and Molecular Biology, Inc. (Jul. 2000).

Smith, L.J., et al., "Human Interleukin 4. The Solution Structure of a Four-helix Bundle Protein," *J. Mol. Biol.* 224:899-904, Academic Press Ltd. (1992).

Smith, D.B., and Johnson, K.S., "Single-step purification of polypeptides expressed in *Escherichia coli* as fusions with glutathione *S*-transferase," *Gene* 67:31-40, Elsevier Science B.V. (1988).

Smith, T.F., and Waterman, M.S., "Comparison of Biosequences," *Adv. Applied Math* 2:482-489, Academic Press, Inc. (1981).

Stroop, S., et al., "Chimeric Human Calcitonin and Glucagon Receptors Reveal Two Dissociable Calcitonin Interaction Sites," *Biochem* 34:1050-1057, American Chemical Society (1995).

Suva, L.J., et al., "A Parathyroid Hormone-Related Protein Implicated in Malignant Hypercalcemia: Cloning and Expression," *Science* 237:983-896, American Association for the Advancement of Science (1987).

Szabo, P., "In Situ Hybridization," in *Human Chromosomes. Manual of Basic Techniques*, Verma, R.S., and Babu, A., eds., Pergamon Press, New York, NY, pp. 152-165 (1989).

Takasu, H., and Bringhurst, F., "Type-1 Parathyroid Hormone (PTH) /PTH-Related Peptide (PTHrP) Receptors Activate Phospholipase C in Response to Carboxyl-Truncated Analogs of PTH(1-34)," *Endocrinology* 139:4293-4299, The Endocrine Society (Oct. 1998).

Tregear, G.W., et al., "Bovine Parathyroid Hormone: Minimum Chain Length of Synthetic Peptide Required for Biological Activity," *Endocrinology* 93:1349-1353, The Endocrine Society (1973).

Tregear, G.W., and Potts, Jr., J.T., "Synthetic Analogues of residues 1-34 of Human Parathyroid Hormone: Influence of Residue Number 1 on Biological Potency *In Vitro*," Endocrine Res. Commun. 2:561-570, Marcel Dekker, Inc. (1975).

Turner, P., et al., "Single Mutations Allow the PTH2 Receptor to respond to PTHrP," *J. Bone Min. Res.* 12:Abs. No. 121, Blackwell Science, Inc. (Aug. 1997).

Turner, P.R., et al., "A Putative Selectivity Filter in the G-protein - coupled Receptors for Parathyroid Hormone and Secretin," *J. Biol. Chem.* 271:9205-9208, The American Society for Biochemistry and Molecular Biology, Inc. (1996).

Turner, P.R., et al., "Transmembrane Residues Together with the Amino Terminus Limit the Response of the Parathyroid Hormone (PTH) 2 Receptor to PTH-related Peptide," *J. Biol. Chem.* 273:3830-3837, The American Society for Biochemistry and Molecular Biology, Inc. (Feb. 1998).

Unson, C., et al., "Characterization of Deletion and Truncation Mutants of the Rat Glucagon Receptor. Seven Transmembrane Segments are Necessary for Receptor Transport to the Plasma Membrane and Glucagon Binding," *J. Biol. Chem.* 270:27720-27727, The American Society for Biochemistry and Molecular Biology, Inc. (1995).

Van Ostade, X., et al., "Human TNF mutants with selective activity on the p55 receptor," *Nature* 361:266-269, Macmillan Magazines Ltd. (1993).

von Heinje, G., "A new method for predicting signal sequence cleavage sites," *Nucl. Acids. Res.* 14:4683-4690, IRL Pres Ltd. (1986).

Wilson, I.A., et al., "The Structure of an Antigenic Determinant in a Protein," *Cell* 37:767-778, MIT (1984).

Zhou, A., et al., "Direct mapping of an agonist-binding domain within the parathyroid hormone/parathyroid hormone-related protein receptor by photoaffinity crosslinking," *Proc. Natl. Acad. Sci. USA* 94:3644-3649, National Academy of Sciences (Apr. 1997).

International Search Report for International Patent Application PCT/US99/27656 (mailed May 3, 2000).

International Search Report for International Patent Application PCT/US99/28207 (mailed Apr. 18, 2000).

International Search Report for International Patent Application PCT/US00/04716, (mailed Oct. 11, 2000).

Dialog File 351, Accession No. 8882525, Derwent WPI English language abstract for European Patent Publication No. EP 0 464 533 (Document AN1), Derwent Information Ltd. (1992).

Bergwitz, C., et al., "Identification, Functional Characterization, and Developmental Expression of Two Nonallelic Parathyroid Hormone (PTH)/PTH-Related Peptide Receptor Isoforms in *Xenopus laevis* (Daudin)," *Endocrinol.* 139:723-732, The Endocrine Society (Feb. 1998).

Bettoun, J.D., et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab.* 82:1031-1040, The Endocrine Society (Apr. 1997).

Bettoun, J.D., et al., "Development Upregulation of Human Parathyroid Hormone (PTH)/PTH-related Peptide Receptor Gene Expression from Conserved and Human-specific Promoters," *J. Clin. Invest.* 102:958-967, The American Society for Clinical Investigation, Inc. (Sep. 1998).

Broadus, A.E., and Stewart, A.F., "Parathyroid Hormone-Related Protein, Structure, Processing, and Physiological Actions," in *The Parathyroids*, Bilezikian, J.P., ed., Raven Press, Ltd., New York, NY, pp. 259-294 (1994).

Gaich, G., et al., "Amino-Terminal Parathyroid Hormone-Related Protein: Specific Binding and Cytosolic Calcium Responses in Rat Insulinoma Cells," *Endocrinol.* 132:1402-1409, The Endocrine Society (1993).

Gardella, T.J., et al., "Converting Parathyroid Hormone-related Peptide (PTHrP) into a Potent PTH-2 Receptor Agonist," *J. Biol. Chem.* 271:19888-19893, The American Society for Biochemistry and Molecular Biology, Inc. (1996).

Iida-Klein, A., et al., "Truncation of the Carboxyl-terminal Region of the Rat Parathyroid Hormone (PTH)/PTH-related Peptide Receptor Enhances PTH Stimulation of Adenylyl Cyclase but Not Phospholipase C," *J. Biol. Chem.* 270:8458-8465, The American Society for Biochemistry and Molecular Biology, Inc. (1995).

Iida-Klein, A., et al., "Structural Requirements of Parathyroid Hormone/Parathyroid Hormone-Related Peptide Receptors for Phospholipase C Activation and Regulation of Phosphate Uptake," *Miner. Electrolyte Metab.* 21:177-179, S. Karger AG (1995).

Inomata, N., et al., "Characterization of a Novel Parathyroid Hormone (PTH) Receptor with Specificity for the Carboxyl-Terminal Region of PTH-(1-84)," *Endocrinol.* 136:4732-4740, The Endocrine Society (1995).

Jing, S., et al., "GDNF-Induced Activation of the Ret Protein Tyrosine Kinase Is Mediated by GDNFR-α, a Novel Receptor for GDNF," *Cell* 85:1113-1124, Cell Press (1996).

Joun, H., et al., "Tissue-Specific Transcription Start Sites and Alternative Splicing of the Parathyroid Hormone (PTH)/PTH-Related Peptide (PTHrP) Receptor Gene: A New PTH/PTHrP Receptor Splice Variant that Lacks the Signal Peptide," *Endocrinol.* 138:1742-1749, The Endocrine Society (Apr. 1997).

Karaplis, A.C., et al., "Lethal skeletal dysplasia from targeted disruption of the parathyroid hormone-related peptide gene," *Genes & Devel.* 8:277-289, Cold Spring Harbor Laboratory Press (1994).

Kong, X.-F., et al., "The Rat, Mouse and Human Genes Encoding the Receptor for Parathyroid Hormone and Parathyroid Hormone-related Peptide are Highly Homologous," *Biochem. Biophys. Res. Comm.* 200:1290-1299, Academic Press (1994).

Kovacs, C.S., et al., "Parathyroid hormone-related peptide (PTHrP) regulates fetal-placental calcium transport through a receptor distinct from the PTH/PTHrP receptor," *Proc. Natl. Acad. Sci. USA* 93:15233-15238, National Academy of Sciences (1996).

Orloff, J.J., et al., "Analysis of PTHRP binding and signal transduction mechanisms in benign and malignant squamous cells," *Amer. J. Physiol.* 262:E599-E607, American Physiological Society (1992).

Orloff, J.J., et al., "A Midregion Parathyroid Hormone-Related Peptide Mobilizes Cytosolic Calcium and Stimulates Formation of Inositol Triphosphate in a Squamous Carcinoma Cell Line," *Endocrinol.* 137:5376-5385, The Endocrine Society (1996).

Orloff, J.J, et al., "Further Evidence for a Novel Receptor for Amino-Terminal Parathyroid Hormone-Related Protein on Keratinocytes and Squamous Carcinoma Cell Lines," *Endocrinol.* 136:3016-3023, The Endocrine Society (1995).

Potts, Jr., J.T., and Jüppner, H., "Parathyroid Hormone and Parathyroid Hormone-Related Peptide in Calcium Homeostasis, Bone Metabolism, and Bone Development: The Proteins, Their Genes, and Receptors," in *Metabolic Bone Disease*, 3rd Edition, Avioli, L.V., and Krane, S.M., eds., Academic Press, San Diego, CA, pp. 51-94 (1998).

Rubin, D.A., et al., "Molecular Cloning and Expression of Receptors for Parathyroid Hormone (PTH) and PTH-Related (PTHrP) Protein in Zebrafish," *Am. Zool.* 36:97A Abs No. 373, Society for Integrative and Comparative Biology (1996).

Rubin, D.A., and Jüppner, H., "Parathyroid Hormone (PTH)/PTH-Related (PTHRP) Receptor Cloning and In Situ Hybridization in the Zebrafish *Danio rerio*," *Am. Zool.* 37:181A Abs. No. 651, Society for Integrative and Comparative Biology (1997).

Schipani, E., et al., "Indentical Complementary Deoxyribonucleic Acids Encode a Human Renal and Bone Parathyroid Hormone (PTH)/PTH-Related Peptide Receptor," *Endocrinol.* 132:2157-2165, The Endocrine Society (1993).

Schipani, E., et al., "Pseudohypoparathyroidism Type Ib Is not Caused by Mutations in the Coding Exons of the Human Parathyroid Hormone (PTH)/PTH-Related Peptide Receptor Gene," *J. Clin. Endocrinol. Metab.* 80:1611-1621, The Endocrine Society (1995).

Sutcliffe, J.G., et al., "Antibodies That React with Predetermined Sites on Proteins,"*Science* 219:660-666, American Association for the Advancement of Science (1983).

Takasu, H., et al., "The 69-84 Amino Acid Region of the Parathyroid Hormone Molecule Is Essential for the Interaction of the Hormone with the Binding Sites with Carboxyl-Terminal Specificity," *Endocrinol.* 137:5537-5543, The Endocrine Society (1996).

Takasu, H., et al., "Human PTH/PTHrP receptors and Type-2 PTH Receptors Show Discordant Selectivity for Human PTH Analogs with Amino-Terminal Modifications," *Bone* 23:S255, Abstract No. T223, Elsevier Science (Nov. 1998).

Treanor, J.J.S., et al., "Characterization of a multicomponent receptor for GDNF," *Nature* 382:80-83, Macmillan Journals Ltd. (1996).

Voet, D., and Voet, J.G., "A. Sickle-Cell Anemia: The Influence of Natural Selection," and "3. Abnormal Hemoglobins," in *Biochemistry*, Voet, D., and Voet, J.G., eds., John Wiley & Sons, Inc., New York, NY, pp. 126-128 and 228-234 (1990).

Wu, T.L., et al., "Structural and Physiologic Characterization of the Mid-region Secretory Species of Parathyroid Hormone-related Protein," *J. Biol. Chem. 271*:24371-24381, The American Society for Biochemistry and Molecular Biology, Inc. (1996).

Yamamoto, S., et al., "Centrally Administered Parathyroid Hormone (PTH)-Related Protein (1-34) But Not PTH(1-34) Stimulates Arginine-Vasopressin Secretion and Its Messenger Ribonucleic Acid Expression in Supraoptic Nucleus of the Conscious Rats," *Endocrinol. 138*:383-388, The Endocrine Society (Jan. 1998).

Yamamoto, S., et al., "Parathyroid Hormone-Related Peptide-(1-34) [PTHrP-(1-34)] Induces Vasopressin Release from the Rat Supraoptic Nucleus *in Vitro* through a Novel Receptor Distinct from a Type I or Type II PTH/PTHrP Receptor," *Endocrinol. 138*:2066-2072, The Endocrine Society (May 1997).

* cited by examiner

```
         ATGGGGGCCGCCCGGATCGCACCCAGCCTGGCGCTCCTACTCTGCTGCCCAGTGCTCAGC
a        M  G  A  A  R  I  A  P  S  L  A  L  L  L  C  C  P  V  L  S   -

TCCGCATATGCGCTGGAGGTATTTGACCGCCTAGGCATGATCTACACCGTGGGATACTCC
a        S  A  Y  A  L  E  V  F  D  R  L  G  M  I  Y  T  V  G  Y  S   -

ATGTCTCTCGCCTCCCTCACGGTGGCTGTGCTCATCCTGGCCTATTTTAGGCGGCTGCAC
a        M  S  L  A  S  L  T  V  A  V  L  I  L  A  Y  F  R  R  L  H   -

TGCACGCGCAACTACATCCACATGCACATGTTCCTGTCGTTTATGCTGCGCGCCGCGAGC
a        C  T  R  N  Y  I  H  M  H  M  F  L  S  F  M  L  R  A  A  S   -

ATCTTCGTGAAGGACGCTGTGCTCTACTCTGGCTTCACGCTGGATGAGGCCGAGCGCCTC
a        I  F  V  K  D  A  V  L  Y  S  G  F  T  L  D  E  A  E  R  L   -

ACAGAGGAAGAGTTGCACATCATCGCGCAGGTGCCACCTCCGCCGGCCGCTGCCGCCGTA
a        T  E  E  E  L  H  I  I  A  Q  V  P  P  P  P  A  A  A  A  V   -

GGCTACGCTGGCTGCCGCGTGGCGGTGACCTTCTTCCTCTACTTCCTGGCTACCAACTAC
a        G  Y  A  G  C  R  V  A  V  T  F  F  L  Y  F  L  A  T  N  Y   -

TACTGGATCCTGGTGGAGGGGCTGTACTTGCACAGCCTCATCTTCATGGCCTTTTTCTCA
a        Y  W  I  L  V  E  G  L  Y  L  H  S  L  I  F  M  A  F  F  S   -

GAGAAGAAGTACCTGTGGGGCTTCACCATCTTTGGCTGGGGTCTACCGGCTGTCTTCGTG
a        E  K  K  Y  L  W  G  F  T  I  F  G  W  G  L  P  A  V  F  V   -

GCTGTGTGGGTCGGTGTCAGAGCAACCTTGGCCAACACTGGGTGCTGGGATCTGAGCTCC
a        A  V  W  V  G  V  R  A  T  L  A  N  T  G  C  W  D  L  S  S   -

GGGCACAAGAAGTGGATCATCCAGGTGCCCATCCTGGCATCTGTTGTGCTCAACTTCATC
a        G  H  K  K  W  I  I  Q  V  P  I  L  A  S  V  V  L  N  F  I   -

CTTTTTATCAACATCATCCGGGTGCTTGCCACTAAGCTTCGGGAGACCAATGCGGGCCGG
a        L  F  I  N  I  I  R  V  L  A  T  K  L  R  E  T  N  A  G  R   -
```

```
    TGTGACACCAGGCAGCAGTACCGGAAGCTGCTCAGGTCCACGTTGGTGCTCGTGCCGCTC
a   C  D  T  R  Q  Q  Y  R  K  L  L  R  S  T  L  V  L  V  P  L   -

TTTGGTGTGCACTACACCGTCTTCATGGCCTTGCCGTACACCGAGGTCTCAGGGACATTG
a   F  G  V  H  Y  T  V  F  M  A  L  P  Y  T  E  V  S  G  T  L   -

TGGCAGATCCAGATGCATTATGAGATGCTCTTCAACTCCTTCCAGGGATTTTTTGTTGCC
a   W  Q  I  Q  M  H  Y  E  M  L  F  N  S  F  Q  G  F  F  V  A   -

ATCATATACTGTTTCTGCAATGGTGAGGTGCAGGCAGAGATTAGGAAGTCATGGAGCCGC
a   I  I  Y  C  F  C  N  G  E  V  Q  A  E  I  R  K  S  W  S  R   -

TGGACACTGGCGTTGGACTTCAAGCGCAAAGCACGAAGTGGGAGTAGCAGCTACAGCTAT
a   W  T  L  A  L  D  F  K  R  K  A  R  S  G  S  S  S  Y  S  Y   -

GGCCCAATGGTGTCTCACACGAGTGTGACCAATGTGGGCCCCCGTGCAGGACTCAGCCTC
a   G  P  M  V  S  H  T  S  V  T  N  V  G  P  R  A  G  L  S  L   -

CCCCTCAGCCCCCGCCTGCCTCCTGCCACTACCAATGGCCACTCCCAGCTGCCTGGCCAT
a   P  L  S  P  R  L  P  P  A  T  T  N  G  H  S  Q  L  P  G  H   -

GCCAAGCCAGGGGCTCCAGCCACTGAGACTGAAACCCTACCAGTCACTATGGCGGTTCCC
a   A  K  P  G  A  P  A  T  E  T  E  T  L  P  V  T  M  A  V  P   -

AAGGACGATGGATTCCTTAACGGCTCCTGCTCAGGCCTGGATGAGGAGGCCTCCGGGTCT
a   K  D  D  G  F  L  N  G  S  C  S  G  L  D  E  E  A  S  G  S   -

GCGCGGCCGCCTCCATTGTTGCAGGAAGGATGGGAAACAGTCATGTGACTGGGCACTAGG
3579 -+----------+----------+----------+----------+----------+-------- 3638
a    A  R  P  P  P  L  L  Q  E  G  W  E  T  V  M  *                 -
```

SCREENING ASSAY UTILIZING THE PTH RECEPTOR

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention is related to the fields of molecular biology, developmental biology, physiology, neurobiology, endocrinology and medicine.

2. Related Art

PTH is the principal regulator of blood calcium levels and mediates this action through binding to PTH-1 receptors on bone and kidney cells (Kronenberg, H. M., et al., in "Handbook of Experimental Pharmacology, Springer-Verlag," Heidelberg (1993)). This receptor also responds to PTH-related peptide, a factor which plays a role in embryonic bone development and is the causative agent of hypercalcemia of malignancy (Lanske, B., et al., Science 273: 663–666 (1996)). PTH and PTHrP peptides have been shown to have potent anabolic effects on bone, and it is possible, therefore, that PTH-1 receptor agonists could ultimately be used to treat metabolic bone diseases, such as osteoporosis (Dempster, D. W., et al., Endocr Rev. 14(6): 690–709 (1994)).

In the fully bioactive PTH(1–34) peptide, the major determinants of receptor-binding affinity reside within amino acids 15 to 34 (Nussbaum, S. R., et al., J. Biol. Chem. 255:10183–10187 (1980); Gardella, T. J., et al., Endocrinology 132(5):2024–2030 (1993); Caulfield, M. P., et al., Endocrinology 127:83–87 (1990); Abou-Samra, A. B., et al., Endocrinology 125:2215–2217 (1989)), which are moderately conserved among PTHs and PTHrPs from various species (Suva, L. J., et al., Science 237(4817):893–896 (1987)). The determinants of receptor activation lie within the more stringently conserved amino-terminal residues, and deletion of these residues yields competitive PTH-1 receptor antagonists (Horiuchi, N., et al., Science 220:1053–1055 (1983); Nutt, R. F., et al., Endocrinology 127:491–493 (1990)). Amino-terminal PTH or PTHrP fragments shorter in length than PTH(1–27) have not previously been found to be biologically active (Rosenblatt, M., Pathobilogy Annual, Raven Press, New York, 11:53–84 (1981); Azarani, A., et al., J. Biol. Chem. 271(25):14931–14936 (1996); Tregear, G. W., et al., Endocrinology 93:1349–1353 (1973)), yet the functional importance and evolutionary conservation of the amino-terminal residues predicts that they directly interact with the receptor.

The PTH-1 receptor couples strongly to the adenylyl cyclase/protein kinase A signaling pathway and, in some settings, to other pathways including those mediated by phospholipase C/protein kinase C and intracellular calcium (About-Samra, A. B., et al., Endocrinology 129:2547–2554 (1991); Jüppner, H., et al., Science 254:1024–1026 (1991); Guo, J. et al., Endocrinology 136:3884–3891 (1995); Hruska, K. A., et al., J. Clin. Invest. 79:230–239 (1987); Donahue, H. J., et al., J. Biol. Chem. 263:13522–13527 (1988)). The PTH-1 receptor is a member of the family B subgroup of G protein-coupled receptors, which also includes the receptors for calcitonin and secretin (Kolakowski, L. F., "GCRDb: A G-Protein-Coupled Receptor Database," Receptors and Channels 2:1–7 (1994)). Mutagenesis and crosslinking studies have indicated that multiple domains of these receptors contribute to ligand interaction, including the large amino-terminal extracellular domain, the extracellular loops and the transmembrane helices (Jüppner, H., et al., Endocrinology 134:879–884 (1994); Lee, C., et al., Mol. Endo. 9:1269–1278 (1995); Turner, P., et al., J. Bone Min. Res. 12(1):Abstract 121 (1997); Dautzenberg, F., et al., Proc. Natl. Acad. Sci. 95:4941–4946 (1998); Holtmann, M., et al., J. Biol. Chem. 270:14394–14398 (1995); DeAlmeida, V. and Mayo, K., Mol. Endo. 12:750–765 (1998); Stroop, S., et al., Biochem. 34:1050–1057 (1994); Zhou, A., et al., Proc. Natl. Acad. Sci. USA 94:3644–3649 (1997); Bisello, A., et al., J. Biol. Chem. 273:22498–22505 (1998)). Studies using PTH/calcitonin chimeric receptors and hybrid ligands have suggested a general topology of the interaction in which the amino-terminal extracellular domain of the receptor recognizes the carboxyl-terminal binding domain of the ligand, while the "core" region of the receptor containing the seven transmembrane helices and connecting loops recognizes the amino-terminal signaling portion of the ligand (Bergwitz, C., et al., J. Biol. Chem. 271:26469–26472 (1996)). Similar conclusions were derived from earlier receptor chimera studies (Jüppner, H., et al., Endocrinology 134:879–884 (1994); Stroop, S., et al., Biochem. 34:1050–1057 (1994); Gardella, T. J., et al., Endocrinology 135:1186–1194 (1994)) and from recent crosslinking studies with photoreactive PTH analogs (Bisello, A., et al., J. Biol. Chem. 273:22498–22505 (1998); Mannstadt, M., et al., J. Biol. Chem. 273:16890–16896 (1998)).

In the current study we investigate the signaling component of the interaction between PTH and the PTH-1 receptor using a domain-based approach. This approach employs short amino-terminal PTH fragment analogs and a PTH receptor mutant that lacks most of the amino-terminal extracellular domain. The results of cAMP-signaling assays performed with these smaller ligands and receptors demonstrate that the conserved amino-terminal (Kronenberg, H. M., et al., in "Handbook of Experimental Pharmacology, Springer-Verlag," Heidelberg (1993); Lanske, B., et al., Science 273:663–666 (1996); Dempster, D. W., et al., Endocr Rev. 14(6):690–709 (1994); Nussbaum, S. R., et al., J. Biol. Chem. 255:10183–10187 (1980); Gardella, T. J., et al., Endocrinology 132(5):2024–2030 (1993); M. P. Caulfield et al., Endocrinology 127:83–87 (1990); A. B. Abou-Samra et al., Endocrinology 125:2215–2217 (1989); Suva, L. J., et al., Science 237(4817):893–896 (1987); Horiuchi, N., et al., Science 220:1053–1055 (1983); Nutt, R. F., et al., Endocrinology 127:491–493 (1990); Rosenblatt, M., Pathobilogy Annual, Raven Press, New York, 11:53–84 (1981); Azarani, A., et al., J. Biol. Chem. 271(25):14931–14936 (1996); Tregear, G. W., et al., Endocrinology 93:1349–1353 (1973); About-Samra, A. B., et al., Endocrinology 129:2547–2554 (1991)) segment of PTH functions as an autonomous signaling domain and that this domain interacts with the core region of the receptor.

SUMMARY OF THE INVENTION

PTH is the principal regulator of blood calcium levels and mediates this action through binding to PTH-1 receptors on bone and kidney cells. PTH-1 receptor agonists may ultimately be used to treat metabolic bone diseases, such as osteoporosis. Thus there is a strong need in the art develop new and improved PTH and PTH receptor reagents for the treatment of human disease.

In a first embodiment, the invention provides a novel PTH-1 receptor polypeptide, rΔNt, characterized by a deletion of the extracellular amino-terminal ligand binding domain. The invention also provides nucleic acid molecules encoding the rΔNt receptor polypeptide.

In a second embodiment the rΔNt receptor of the invention is useful for screening procedures designed to identify agonists and antagonists of PTH receptor function. The invention provides screening utilizing either cAMP accumulation or competitive binding for the evaluation of test compounds with cells expressing the rΔNt receptor.

BRIEF DESCRIPTION OF THE FIGURES

FIG. 1. Presentation of the nucleic acid sequence (SEQ ID NO:1) and the amino acid sequence (SEQ ID NO:2) of the mutant PTH1R receptor, rΔNt.

DETAILED DESCRIPTION OF THE PREFERRED EMBODIMENTS

Figures 2A, 2B:
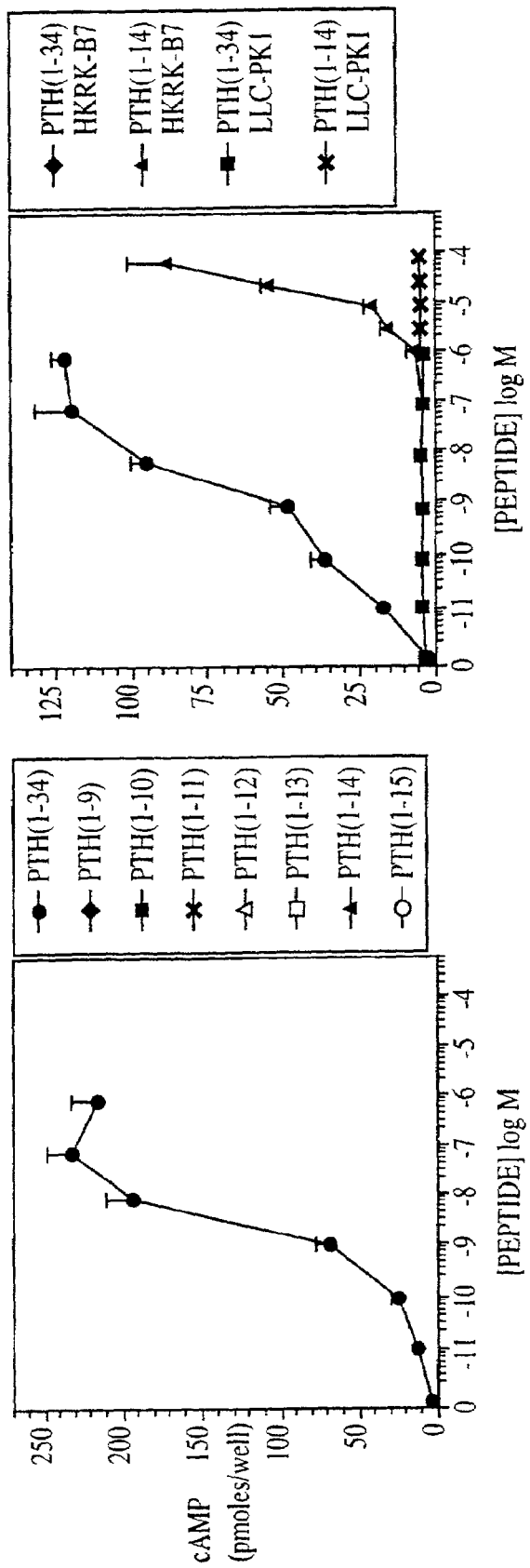
FIG. 2. cAMP-stimulating Activity of PTH Fragments in LLC-PK1 Cells. A) Rat PTH(1–34) analog or amino-terminal rPTH fragments were tested for cAMP-stimulating activity in an LLC-P1-derived cell line (HKRK-B7) stably transfected with the human PTH-1 receptor. Cells were treated with peptide at the indicated doses for 60 min at 22° C. Intracellular cAMP was measured by RIA, as described in Experimental Procedures. Shown are combined data (mean±s.e.m.) from 3 separate experiments, each performed in duplicate. B) HKRK-B7 cells, or untransfected LLC-PK1 were treated with rPTH(1–34) or rPTH(1–14), and intracellular cAMP was measured. Shown are data (mean±s.e.m.) from a single representative experiment performed in duplicate.

The present invention provides isolated nucleic acid molecules comprising a polynucleotide encoding the rΔNt receptor polypeptide, a novel, mutant PTH1R receptor polypeptide, having the amino acid sequence shown in FIG. 1 (SEQ ID NO:2), which was determined by sequencing a cloned cDNA. The rΔNt protein of the present invention shares sequence homology with previously identified non-mutant PTH1R and PTH2R sequences. The nucleotide sequence shown in FIG. 1 (SEQ ID NO:1) was obtained by sequencing a cDNA clone (rΔNt), which was deposited on Dec. 28, 1999 at the American Type Culture Collection, 10801 University Boulevard, Manassas, Va. 20110-2209, and given accession number PTA-1136.

1. The rΔNt Receptor a) Nucleic Acid Molecules

Unless otherwise indicated, all nucleotide sequences determined by sequencing a DNA molecule herein were determined by manual sequencing, and all amino acid sequences of polypeptides encoded by DNA molecules determined herein were predicted by translation of a DNA sequence determined as above. Therefore, as is known in the art for any DNA sequence determined by this approach, any nucleotide sequence determined herein may contain some errors. Nucleotide sequences determined by manual sequencing are typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1, a nucleic acid molecule of the present invention encoding a rΔNt polypeptide, respectively, may be obtained using standard techniques. Cloning and screening procedures are known for the isolation of the wild-type PTH1R sequence, such as those for cloning cDNAs using mRNA as starting material. Subsequent to cloning the wild-type receptor, the appropriate deletion in the sequence may be made as described herein. Illustrative of the invention, the nucleic acid molecule described in FIG. 1 (SEQ ID NO:1) was obtained by using standard restriction enzyme digestion and cloning techniques in the art. The determined nucleotide sequence of the rΔNt cDNA of FIG. 1 (SEQ ID NO:1) contains an open reading frame encoding a protein of about 435 amino acid residues, with a predicted leader sequence of about 22 amino acid residues. The amino acid sequence of the predicted mature rΔNt receptor is shown in FIG. 1 from amino acid residue about 23 to residue about 435. The rΔNt protein shown in FIG. 1 (SEQ ID NO:2) is about 84% identical to the rat PTH 1 receptor.

As indicated, the present invention also provides the mature form(s) of the rΔNt receptor of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature rΔNt polypeptides having the amino acid sequence encoded by the cDNA clone contained in the host identified as ATCC Deposit No. PTA-1136 and as shown in FIG. 1 (SEQ ID NO:2). By the mature rΔNt protein having the amino acid sequence encoded by the cDNA clone contained in the host identified as ATCC Deposit PTA-1136 is meant the mature form(s) of the rΔNt receptor produced by expression in a mammalian cell (e.g., COS cells, as described below) of the complete open reading frame encoded by the DNA sequence of the clone contained in the vector in the deposited host. As indicated below, the mature rΔNt receptor having the amino acid sequence encoded by the cDNA clone contained in ATCC Deposit No. PTA-1136 may or may not differ from the predicted "mature" rΔNt protein shown in FIG. 1 (amino acids from about 23 to about 435) depending on the accuracy of the predicted cleavage.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein. A computational method may be found in the computer program "PSORT" (K. Nakai and M. Kanehisa, Genomics 14:897–911 (1992)), which is an expert system for predicting the cellular location of a protein based on the amino acid sequence. As part of this computational prediction of localization, the methods of McGeoch and von Heinje are incorporated.

In the present case, the predicted amino acid sequence of the complete rΔNt polypeptide of the present invention was analyzed for structural properties by comparison to the rat rΔNt sequence. This analysis provided predicted a cleavage site between amino acids 22 and 23 in FIG. 1 (SEQ ID NO:2). Thus, the leader sequence for the rΔNt receptor protein is predicted to consist of amino acid residues 1–22 in FIG. 1 (amino acids 1 to 22 in SEQ ID NO:2), while the predicted mature rΔNt protein consists of residues 23–435 (amino acids 23 to 435 in SEQ ID NO:2).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

As one of ordinary skill would appreciate, however, due to the possibilities of sequencing errors, the rΔNt receptor polypeptide encoded by the deposited cDNA comprises about 435 amino acids, but may be anywhere in the range of 425–435 amino acids; and the leader sequence of this protein is about 22 amino acids, but may be anywhere in the range of about 10 to about 30 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIG. 1 (SEQ ID NO:1); DNA molecules comprising the coding sequence for the rΔNt receptor shown in FIG. 1 (SEQ ID NO:2); and DNA molecules which comprise a sequence substantially different from those described above but which, due to the degeneracy of the genetic code, still encode the rΔNt receptor. Of course, the genetic code is well known in the art. Thus, it would be routine for one skilled in the art to generate such degenerate variants.

In another aspect, the invention provides isolated nucleic acid molecules encoding the rΔNt polypeptide having an amino acid sequence encoded by the cDNA clone contained in the plasmid deposited as ATCC Deposit No. PTA-1136 on Dec. 28, 1999. Preferably, the nucleic acid molecule will encode the mature polypeptide encoded by the above-described deposited cDNA clone. In a further embodiment, a nucleic acid molecule is provided encoding the rΔNt polypeptide or the rΔNt polypeptide lacking the N-terminal methionine. The invention also provides an isolated nucleic acid molecule having the nucleotide sequence shown in SEQ ID NO:1 or the nucleotide sequence of the rΔNt cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the rΔNt gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNAs or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of about 50–1550 nt in length, and more preferably at fragments least about 600 nt in length are also useful according to the present invention as are fragments corresponding to most, if not all, of the nucleotide sequence of the deposited cDNAs or as shown in FIG. 1 (SEQ ID NO:1). By a fragment at least 20 nt in length, for example, is intended fragments which include 20 or more contiguous bases from the nucleotide sequence of the deposited cDNAs or the nucleotide sequence as shown in FIG. 1 (SEQ ID NO:1).

Preferred nucleic acid fragments of the present invention include nucleic acid molecules encoding: a polypeptide comprising the rΔNt receptor extracellular domain (predicted to constitute amino acid residues from about 23 to about 147 in FIG. 1 (or amino acid residues from about 23 to about 147 in SEQ ID NO:2)); a polypeptide comprising the rΔNt receptor transmembrane domain (predicted to constitute amino acid residues from about 148 to about 416 in FIG. 1 (or amino acid residues from about 148 to about 416 in SEQ ID NO:2)); and a polypeptide comprising the rΔNt receptor extracellular domain with all or part of the transmembrane domain deleted. As above with the leader sequence, the amino acid residues constituting the rΔNt receptor extracellular and transmembrane domains have been predicted. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding epitope-bearing portions of the rΔNt receptor protein. As one skilled in the art would know, a nucleic acid sequence may be used to predict the polypeptide sequence encoded therein. Such information may then be used to predict antigenic determinants in the polypeptide that may be related to the corresponding polynucleotide regions encoding the antigenic determinants identified by the analysis. Methods for predicting the antigenic determinants of a polypeptide are well known in the art.

Methods for determining other such epitope-bearing portions of the rΔNt, protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposit Nos. PTA-1136, PTA-1138, PTA-1139, PTA-1140, PTA-1142, PTA-1137 or PTA-1141. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in FIG. 1 (SEQ ID NO:1).

Of course, a polynucleotide which hybridizes only to a poly A sequence (such as the 3N terminal poly(A) tract of the rΔNt receptor cDNA shown in FIG. 1 (SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a rΔNt polypeptide may include, but are not limited to those encoding the amino acid sequence of the mature polypeptides, by themselves; the coding sequence for the mature polypeptides and additional sequences, such as those encoding the amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5N and 3N sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the rΔNt receptor fused to Fc at the amino or C-terminus.

The present invention further relates to variants of the nucleic acid molecules of the present invention, which encode portions, analogs or derivatives of the rΔNt receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the rΔNt receptor or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to (a) a nucleotide sequence encoding the full-length rΔNt polypeptide having the complete amino acid sequence in SEQ ID NO:2, including the predicted leader sequence; (b) a nucleotide sequence encoding the polypeptide having the amino acid sequence in SEQ ID NO:2, but lacking the N-terminal methionine; (c) a nucleotide sequence encoding the mature rΔNt receptor (full-length polypeptide with the leader removed) having the amino acid sequence at positions from about 23 to about 435 in SEQ ID NO:2; (d) a nucleotide sequence encoding the full-length rΔNt polypeptide having the complete amino acid sequence including the leader encoded by the cDNA clone contained in ATCC Deposit No. PTA-1136; (e) a nucleotide sequence encoding the mature rΔNt receptor having the amino acid sequence encoded by the cDNA clone contained in ATCC Deposit No. 97883; (f) a nucleotide sequence encoding the rΔNt receptor extracellular domain; (g) a nucleotide sequence encoding the rΔNt receptor transmembrane domain; (h) a nucleotide sequence encoding the rΔNt receptor extracellular domain with all or part of the transmembrane domain deleted; and (i) a nucleotide sequence complementary to any of the nucleotide sequences in (a), (b), (c), (d), (e), (f), (g) or (h).

By a polynucleotide having a nucleotide sequence at least, for example, 95% "identical" to a reference nucleotide sequence encoding a rΔNt polypeptide is intended that the nucleotide sequence of the polynucleotide is identical to the reference sequence except that the polynucleotide sequence may include up to five point mutations per each 100 nucleotides of the reference nucleotide sequence encoding the rΔNt receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5N or 3N terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in FIG. 1 or to the nucleotides sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in FIG. 1 (SEQ ID NO:1) or to the nucleic acid sequence of the deposited cDNAs, irrespective of whether they encode a polypeptide having rΔNt receptor activity. This is because even where a particular nucleic acid molecule does not encode a polypeptide having rΔNt receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having rΔNt receptor activity include, inter alia, (1) isolating the rΔNt receptor gene or allelic variants thereof in a cDNA library; (2) in situ hybridization (e.g., "FISH") to metaphase chromosomal spreads to provide precise chromosomal location of the rΔNt receptor gene, as described in Verma et al., *Human Chromosomes: A Manual of Basic Techniques*, Pergamon Press, New York (1988); and (3) Northern Blot analysis for detecting rΔNt receptor mRNA expression in specific tissues.

Preferred, however, are nucleic acid molecules having sequences at least 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having rΔNt receptor activity. By "a polypeptide having rΔNt receptor activity" is intended polypeptides exhibiting activity similar, but not necessarily identical, to an activity of the rΔNt receptor of the invention, as measured in a particular biological assay. For example, rΔNt receptor activity can be measured using competition binding experiments of labeled PTH or PTHrP to cells expressing the candidate rΔNt polypeptide as described herein.

Any cell line expressing the rΔNt receptor, or variants thereof, may be used to assay ligand binding and second messenger activation as described in Examples 3 and 4. Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNAs or the nucleic acid sequence shown in FIG. 1 (SEQ ID NO:1) will encode a polypeptide "having rΔNt receptor activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having rΔNt protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

b) Vectors and Host Cells

The present invention also relates to vectors which include the isolated DNA molecules of the present invention, host cells which are genetically engineered with the recombinant vectors, and the production of rΔNt polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The rΔNt receptor can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

c) rΔNt Polypeptides and Fragments

The invention further provides an isolated rΔNt polypeptide having the amino acid sequence encoded by the deposited cDNAs, or the amino acid sequence in FIG. 1 (SEQ ID NO:2) or a peptide or polypeptide comprising a portion of the above polypeptides.

It will be recognized in the art that some amino acid sequences of the rΔNt receptor can be varied without significant effect of the structure or function of the protein. If such differences in sequence are contemplated, it should be remembered that there will be critical areas on the protein which determine activity. Thus, the invention further includes variations of the rΔNt receptor which show substantial rΔNt receptor activity or which include regions of rΔNt protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of FIG. 1 (SEQ ID NO:2) or that encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the rΔNt protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the rΔNt receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |

TABLE 1-continued

| Conservative Amino Acid Substitutions. | |
|---|---|
| Acidic | Aspartic Acid |
| | Glutamic Acid |
| Small | Alanine |
| | Serine |
| | Threonine |
| | Methionine |
| | Glycine |

Amino acids in the rΔNt protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the antimicrobial peptide polypeptide can be substantially purified by the one-step method described in Smith and Johnson, *Gene* 67:31–40 (1988).

The polypeptides of the present invention are preferably provided in an isolated form, and preferably are substantially purified. A recombinantly produced version of the rΔNt receptor can be substantially purified by the one-step method described in Smith and Johnson, *Gene* 67:31–40 (1988).

The polypeptides of the present invention also include the polypeptide encoded by the deposited rΔNt cDNA including the leader, the polypeptide encoded by the deposited the cDNA minus the leader (i.e., the mature protein), the polypeptide of FIG. 1 (SEQ ID NO:2) including the leader, the polypeptide of FIG. 1 (SEQ ID NO:2) minus the leader, the extracellular domain, the transmembrane domain, a polypeptide comprising amino acids about 1 to about 435 in SEQ ID NO:2, and a polypeptide comprising amino acids about 2 to about 435 in SEQ ID NO:2, as well as polypeptides which are at least 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a rΔNt polypeptide is intended that the amino acid sequence of the polypeptide is identical to the reference sequence except that the polypeptide sequence may include up to five amino acid alterations per each 100 amino acids of the reference amino acid of the rΔNt receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIG. 1 (SEQ ID NO:2) to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

2. Agonists and Antagonists of the rΔNt Receptor Activity

Functional characterization of the biological properties of the rΔNt receptor of the invention and derivatives thereof may be performed by bioassays that measure ligand-stimulated cAMP accumulation.

A. Assay for the Detection of Cyclic AMP Accumulation in Cells Expressing rΔNt Receptor after Exposure to Test Compounds Intracellular cAMP accumulation is measured as described previously (Abou-Samra et al., *J. Biol. Chem.* 262:1129, 1986). Cells expressing the rΔNt receptor grown in 24-well plates are rinsed with culture medium containing 0.1% BSA and 2 mM IBMX. The cells are then incubated with a test compound for 60 min. at 21° C. The supernatant is removed and the cells immediately frozen by placing the whole plate in dry ice powder. Intracellular cAMP is extracted by thawing the cells in 1 ml of 50 mM HCl and analyzed by a specific radioimmunoassay using an anti-cAMP antibody (e.g., Sigma, St. Louis, Mo.). A cAMP analog (2'-O-monosuccinyl-adenosine 3':5'-cyclic monophosphate tyrosyl methyl ester, obtained from Sigma) which is used a tracer for cAMP is iodinated by the chloramine T method. Free iodine is removed by adsorbing the iodinated cAMP analog onto a C18 SEP-PAK cartridge (Waters, Milford, Mass.). After washing with dH$_2$O, the iodinated cAMP analog is eluted from the SEP-PAK Cartridge with 40% acetonitrille (ACN) and 0.1% trifluoroacetic acid (TFA). The iodinated cAMP analog is lyophilized, reconstituted in 1 ml 0.1% TFA, and injected into a C18 reverse phase HPLC column (Waters). The column is equilibrated with 10% ACN in 0.1% TFA, and eluted with gradient of 10–30% ACN in 0.1% TFA. This allows separation of the mono-iodinated cAMP analog from the non-iodinated cAMP analog. The tracer is stable for up to 4 months when stored at –20° C. The standard used for the assay, adenosine 3':5'-cyclic monophosphate, may be purchased from Sigma. Samples (1–10 82 1 of HCl extracts) or standards (0.04–100 fmol/tube) are diluted in 50 mM Na-acetate (pH 5.5), and acetylated with 10 µl of mixture of triethylamine and acetic anhydride (2:1 vol:vol). After acetylation, cAMP antiserum (100 µl) is added from a stock solution (1:4000) made in PBS (pH 7.4), 5 mM EDTA and 1% normal rabbit serum. The tracer is diluted in PBS (pH 7.4) with 0.1% BSA, and added (20,000 cpm/tube). The assay is incubated at 4° C. overnight. The bound tracer is precipitated by adding 100 µl of goat anti-rabbit antiserum (1:20 in PBS) and 1 ml of 7% polyethyleneglycol (MW 5000–6000), centrifuging at 2000 rpm for 30 min. at 4° C. The supernatant is removed and the bound radioactivity is counted in a gamma-counter (Micromedic). To compute the cAMP data, logit calculations are performed in Excel spreadsheets. Typically, the assay sensitivity is 0.1 fmol/tube, and the standard concentration that displaces 50% of tracer is 5 fmol/tube.

B. Screening Compounds Utilizing an rΔNt Receptor Binding Assay

In addition to the cAMP accumulation assay described below, it is possible that compounds may be iodinated and used in a radioreceptor-based assay in rΔNt transiently transfected COS cells. COS-7 cells are grown in 15 cm plates in DMEM, 10% heat-inactivated FBS, 10 mg/L gentamycin until 80–90% confluent. Twenty-four hours after transfection by the DEAE/Dextran method (Sambrook et al., supra), with 1–2 µg of plasmid DNA, the cells are trypsinized and replated in multiwell plastic dishes (16 or 35 mm diameter, Costar, Cambridge, Mass.) at a cell concentration of 5×10$^4$ cells/cm$^2$. Cell number increased only slightly after transfection. After continuing culture for another 48 h, radioreceptor assays are performed. The culture medium is replaced with buffer containing 50 mM Tris-HCL (pH 7.7), 100 mM NaCl, 2 mM CaCl$_2$, 5 mM KCL, 0.5% heat-inactivated fetal bovine serum (GIBCO), and 5% heat-inactived horse serum (KC Biological Inc., Lenexa, Kans.) immediately before studies are initiated. Unless otherwise indicated, studies are conducted with cells incubated in this buffer at 15° C. for 4 h with 4×10$^5$ cpm/ml (9.6×10$^{-11}$ M) of $^{125}$I-labeled [Ala$^1$]PTH(1–14) amide or $^{125}$I-labeled [Nle$^8$]PTH(1–14).

C. Screening for PTH-1 Receptor Antagonists and Agonists

The rΔNt receptor of the invention may be utilized in to screen for compounds that are agonistic or antagonistic to the PTH response using the cAMP accumulation assay. Cells expressing PTH-1 receptor on the cell surface are incubated with native PTH(1–84) for 5–60 minutes at 37° C., in the presence of 2 mM IBMX (3-isobutyl-1-methyl-xanthine, Sigma, St. Louis, Mo.). Cyclic AMP accumulation is measured by specific radio-immunoassay, as described above. A test compound that competes with native PTH(1–84) for binding to the rΔNt receptor, and that inhibits the effect of native PTH(1–84) on cAMP accumulation, is considered a competitive antagonist. Such a compound would be useful for treating hypercalcemia.

Conversely, a test compound that does not compete with native PTH(1–84) for binding to the rΔNt receptor, but which still prevents native PTH(1–84) activation of cAMP accumulation (presumably by blocking the receptor activation site) is considered a non-competitive antagonist. Such a compound would be useful for treating hypercalcemia.

A candidate compound that competes with native PTH (1–84) for binding to the rΔNt receptor, and which stimulates cAMP accumulation in the presence or absence of native PTH(1–84) is a competitive agonist. A candidate compound that does not compete with native PTH(1–84) for binding to the rΔNt receptor but which is still capable of stimulating cAMP accumulation in the presence or absence of native PTH(1–84), or which stimulates a higher cAMP accumulation than that observed with a PTH compound would be considered a non-competitive agonist.

Thus, in a further aspect, a screening method is provided for determining whether a candidate agonist or antagonist is capable of enhancing or inhibiting a cellular response to PTH or PTHrP. The method involves contacting cells which express the rΔNt polypeptide with a candidate compound and the PTH or PTHrP ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or PTH or PTHrP (e.g., cyclic AMP accumulation). By the invention, a cell expressing the rΔNt polypeptide can be contacted with either an endogenous or exogenously administered PTH or PTHrP.

EXAMPLES

General Methods

Peptides: Peptides were prepared by the Biopolymer Synthesis Facility at Massachusetts General Hospital (Boston, Mass.) using solid-phase chemistry with Fmoc (N-(9-fluorenyl)methoxycarbonyl) protecting groups, and TFA-mediated cleavage and deprotection. All peptides were C-terminally amidated. The PTH(1–14) analogs were synthesized on a multiple peptide synthesizer (Advanced Chemtech Model 396 MBS) at 0.025 mM scale. The completed peptides were desalted by adsorption on a C18 cartridge (Sep-Pak) and then analyzed by reversed-phase C18-based HPLC, MALDI-mass spectromety and amino acid analysis. The PTH(1–34) control peptide, [Nle$^{8,21}$, Tyr$^{34}$]rPTH-(1–34)NH$_2$, and the PTHrP(7–34) antagonist peptide, [Leu$^{11}$,D-Trp$^{12}$]hPTHrP(7–34)NH$_2$, were prepared on an Applied Biosystems Synthesizer (Model 431A) 0.1 mM scale, purified by reversed-phase C18-based HPLC and characterized as described above. Concentrated stock solutions of peptides, 10 mM for PTH(1–14) analogs and 0.3 mM for PTHrP(7–34) and PTH(1–34), were prepared in 10 mM acetic acid, quantified by acid hydrolysis and amino acid analysis and stored at –80° C.

Cell Culture and DNA Transfection: COS-7 and HKRK-B7 cells were cultured at 37° C. in Dulbecco's modified Eagle's medium (DMEM) supplemented with fetal bovine serum (10%); penicillin G (20 units/ml), streptomycin sulfate (20 µg/ml) and amphotericin B (0.05 µg/ml) in a humidified atmosphere containing 5% CO$_2$. Twenty-four to 16 hours prior to assay, cells in 24-well plates were shifted to a humidified incubator containing 5% CO$_2$ that was set at 33° C. Stock solutions of EGTA/trypsin and antibiotics were from GIBCO; fetal bovine serum was from Hyclone Laboratories (Logan, Utah). Derivation and characterization of the HKRK-B7 cell line by stable transfection of LLC-PK$_1$ cells with a pCDNA-1-based plasmid (In Vitrogen, San Diego, Calif.) encoding the hPTH-1 receptor was described previously (Takasu, H. and Bringhurst, F., *Endocrinology*, in press (1998)). These cells express PTH-1 receptors at a surface density of about 1×10$^6$ PTH-binding sites per cell. The HKRK-B7 cells were used for functional assays 24 to 72 hours after the cell monolayer reached confluency.

Figure 3:
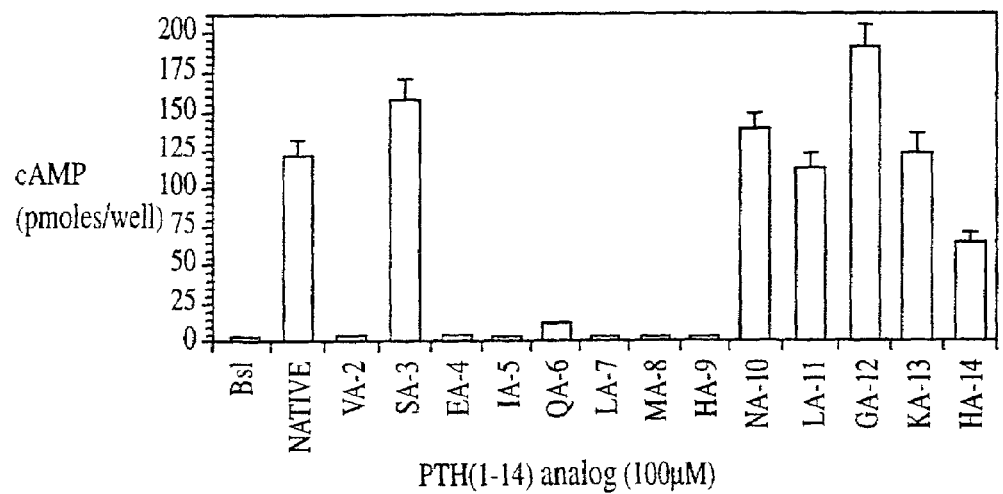
FIG. 3. Alanine-scan of PTH(1–14). HKRK-B7 cells were treated with 100 mM of one of 14 different rPTH(1–14) analogs, each having a different alanine-substitution at the indicated amino acid position. The resulting cAMP levels were determined as described in Experimental Procedures. Shown are the combined data (mean±s.e.m.) from three separate experiments, each performed in duplicate. The mean (mean±s.e.m.) basal cAMP levels observed in the three experiments was 2.1±0.1 pmole/well, and the maximum response to rPTH(1–34) at 0.1 mM was 254±16 pmole/well.

For studies with the intact and truncated rat PTH-1 receptors, transient transfections of COS-7 cells were performed using DEAE-dextran as described previously (Bergwitz, C., et al., *J. Biol. Chem.* 272:28861–28868)). The construction and initial characterization of the pCDNA-1 based plasmids encodin either the intact or truncated rat PTH-1 receptor has been described previously (Lee, C., et al., *Endocrinology* 135(4):1488–1495)). The intact receptor (rWT-HA) contains a nine amino acid HA epitope tag in place of residues 93–101 of the extracellular domain; this epitope tag does not affect receptor function (Lee, C., et al., *Endocrinology* 135(4):1488–1495)). The truncated rat PTH-1 receptor (rΔNt) is deleted for exons E1 through exon G (residues 26 to 181). Assuming that signal peptidase cleavage occurs between Ala-22 and Tyr-23 (Nielsen, H., et al., *Protein Engineering* 10:1–6 (1997)), rΔNt is predicted to have for its N-terminus residues Dautzenberg, F., et al., *Proc. Natl. Acad. Sci.* 95:4941–4946 (1998); Holtmann, M., et al., *J. Biol. Chem.* 270:14394–14398 (1995); DeAlmeida, V. and Mayo, K., *Mol. Endo.* 12:750–765 (1998)) joined to Glu-182 (FIG. 3B). COS-7 cells were transfected in 24-well plates when the cells were 85 to 95% of confluency, using 200 ng of plasmid DNA that was purified by cesium chloride/ethidium bromide gradient centrifugation for each well. Assays were conducted 72 to 96 hours after transfection. Under these conditions about ~20% of the COS-7 cells become transfected and express about 5×10$^6$ surface PTH receptors per cell (Bergwitz, C., et al., *J. Biol. Chem.* 272:28861–28868)).

Intracellular cyclic AMP: Transfected COS-7 or HKRK-B7 cells were rinsed with 500 ml of binding buffer, (50 mM Tris-HCl, pH 7.7, 100 mM NaCl, 5 mM KCl, 2 mM CaCl2, 5% heat-inactivated horse serum, 0.5% heat-inactivated fetal bovine serum) and 200 ml of IBMX buffer (DMEM containing 2 mM IBMX, 1 mg/ml bovine serum albumin, 35 mM Hepes-NaOH, pH 7.4) and 100 ml of binding buffer or binding buffer containing various amounts of peptide were added. The plates were incubated for 60 minutes at room temperature. The buffer was then withdrawn and the cells were frozen on dry ice, treated with 0.5 ml of 50 mM HCl, and refrozen. After the thawing, the lysate was diluted 30-fold in dH20 and an aliquot was analyzed for cAMP content by determined radioimmunoassay using unlabeled cAMP as a standard.

For cAMP inhibition assays, transfected COS-7 cells were rinsed once with 500 ml of binding buffer, and 200 ml of IBMX buffer and 100 ml of binding buffer or binding buffer containing the antagonist [Leu11,D-Trp12]hPTHrP(7–34) NH2 (10 mM) were added. After a 5 minute incubation at room temperature, 10 ml of binding buffer containing PTH (1–14) or PTH(1–34) (agonist peptide) was added, and the incubation was continued for an additional 30 minutes. The cells were then lysed and intracellular cAMP levels were measured as described above.

Example 1

PTH(1–14) Action in Stable Cells

Amino-terminal peptide fragments based on the rat PTH sequence and ranging in length from PTH(1–9) to PTH (1–15) were synthesized and tested for activity in an LLC-PK1-derived cell line called HKRK-B7 which stably expresses high levels (1×10$^6$ receptors/cell) of the cloned human PTH-1 receptor (Takasu, H. and Bringhurst, F.,

*Endocrinology*, in press (1998)). As shown in FIG. 1A, the intact control peptide PTH(1–34) mediated a 50-fold increase in intracellular cAMP levels relative to the basal cAMP level, and the estimated EC50 for this response was ~2 nM with PH(1–13) and shorter fragments little or no increase in cAMP accumulation was observed (FIG. 1A). However, two of the amino-terminal fragments, PTH(1–14) and PTH(1–15), stimulated cAMP formation to about 20-fold over the basal level, although the doses required for this activation were five to six orders of magnitude higher than the dose required for PTH(1–34). The response to these active peptides was dependent on the transfected PTH receptor, as parental LLC-PK1 cells, which do not express PTH receptors, but do express the related calcitonin receptor, were unresponsive to PTH(1–34) or PTH(1–14) (FIG. 2B).

With the intact receptor, the potency of PTH(1–14) was about five orders of magnitude weaker than that of PTH (1–34). This reduced potency is not surprising, given that the PTH(1–14) peptide lacks important receptor-binding residues located in the PTH(15–34) region in the PTH(15–34) domain (Nussbaum, S. R., et al., *J. Biol. Chem.* 255: 10183–10187 (1980); Gardella, T. J., et al., *Endocrinology* 132(5):2024–2030 (1993); Caulfield, M. P., et al., *Endocrinology* 127:83–87 (1990); and Abou-Samra, A.-B., et al., *Endocrinology* 125:2215–2217 (1989)). Consistent with this, unlabeled PTH(1–14) bound too weakly to permit detection in our standard competition binding assays which used radioiodinated rPTH(1–34) as a tracer ligand, nor could we detect direct binding of radiolabled PTH(1–14) analog to the intact or truncated receptors used in this study (data not shown).

Example 2

Alanine Scanning of PTH(1–14)

To identify residues in the PTH(1–14) fragment that play a role in activating the adenylyl cyclase-signaling pathway, an alanine-scanning approach was employed. Thirteen different alanine-substituted rat PTH(1–14) analogs were synthesized and tested for the ability to stimulate cAMP formation in HKRK-B7 cells (FIG. 2). The activity profile obtained with the monosubstituted analogs revealed that residues in the 1–9 region formed a relatively intolerant segment of the peptide, whereas residues in the 10–14 region formed a comparatively tolerant segment. Thus, with the exception of Ser-3 and Ala-1 (which is the native amino-terminal residue of rat PTH) most alanine substitutions in the 1–9 region yielded peptides that were barely active or inactive. In contrast, each alanine substitution in the 10–14 region yielded peptides with activities comparable with that of native rat PTH(1–14). The activity of the alanine-3 substituted peptide correlates well with previous studies on PTH(1–34) analogs which showed that amino acids with small side chains are tolerated at this site (Cohen, F. E., et al., *J. Biol. Chem.* 266:1997–2004 (1991)).

Example 3

Potentcy of the rΔNt Receptor with Small Ligands

Figure 4A:
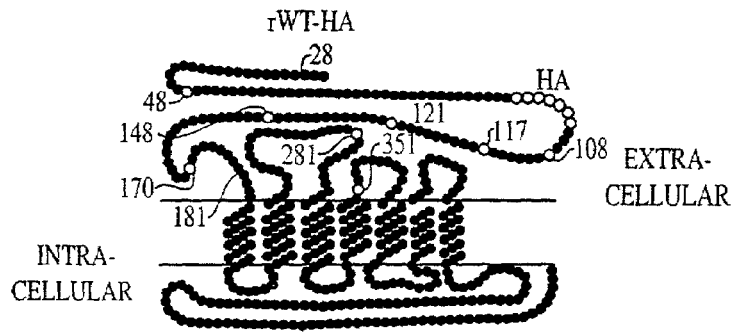
FIG. 4. PTH Responses of Intact and Truncated PTH-1 Receptors in COS-7 Cells. Shown at the top are schematics of the intact (A) and truncated (B) rat PTH-1 receptors used for transient transfection of COS-7 cells, and subsequent cAMP response assays. The conserved extracellular cysteine residues are depicted as open circles and numbered according to sequence position, and the nine amino acids of the epitope tag (HA) in rWT-HA are shaded. The tics at residue 26 and 181 indicate the endpoints of the deletion in rΔNt. Based on the predicted signal peptide cleavage site at Ala-22, residues 23–25 in rΔNt are joined to residue 182. The cAMP responses of COS-7 cells expressing the intact receptor (C) and rΔNt (D) to rPTH(1–34) (J) or rPTH(1–14) (C) are also shown. The graphs show combined data (mean±s.e.m.) from five separate experiments, each performed in duplicate.
Figure 4B:
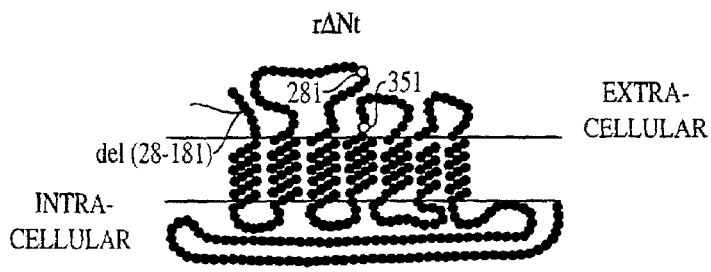
Figures 4C, 4D:
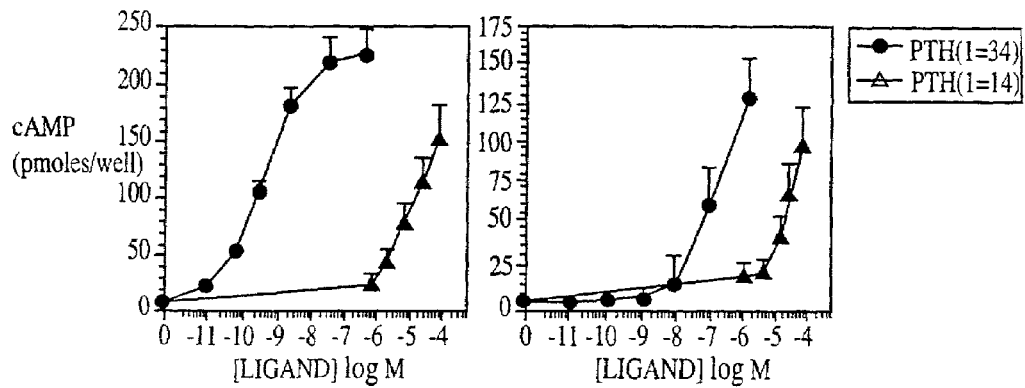

Experiments utilized COS-7 cells transfected with either the intact rat PTH-1 receptor (rWT-HA, FIG. 4A) or a truncated rat PTH-1 receptor with most of the amino-terminal extracellular domain deleted (rΔNt, FIG. 4B). In COS-7 cells expressing rWT-HA, PTH(1–34) and PTH (1–14) mediated cAMP responses that were similar to the responses seen in HKRK-B7 cells: PTH(1–14) stimulated a 15-fold in cAMP formation, but with a potency that was four to five orders of magnitude weaker than that of PTH(1–34) (FIG. 3C). Both peptides also stimulated cAMP formation in cells transfected with rΔNt, but the potency of PTH(1–14) was only two orders of magnitude weaker than that of PTH(1–34) with this truncated receptor (FIG. 3D). This change in the relative potency of the two ligands could be accounted for by a 100-fold decrease in the potency which PTH(1–34) exhibited with rΔNt, as compared to its potency with rWT-HA, rather than a shift in the potency of PTH (1–14), which was equipotent with the two receptors (compare panels C and D of FIG. 4).

Figure 7A:
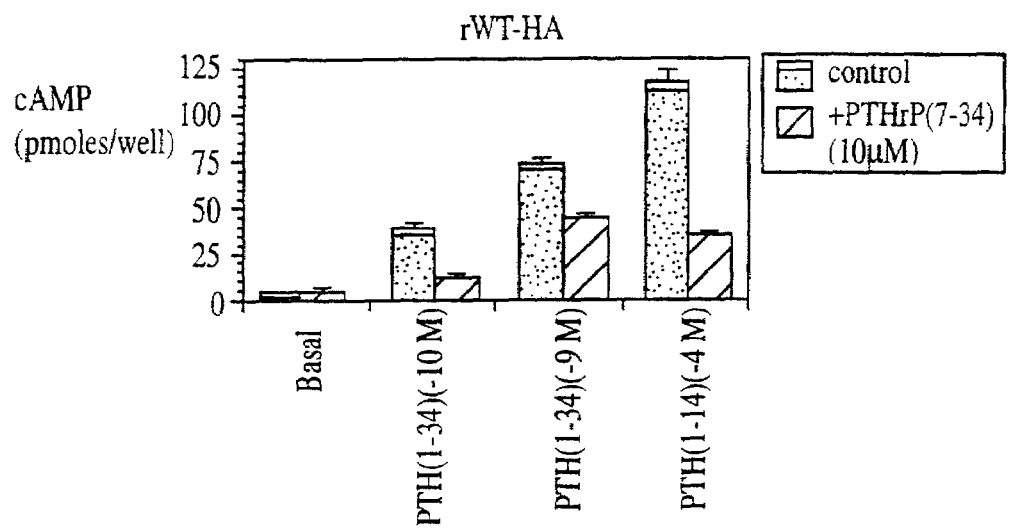
FIG. 7. Antagonist Properties of PTHrP(7–34) with PTH (1–14). COS-7 cells transfected with rWT-HA (A) or rΔNt (B) were treated with the antagonist [Leu11,D-Trp12] hPTHrP(7–34)NH2 (or buffer alone), for 5 min at 22EC, followed by 10 ml of either rPTH(1–34) or rPTH(1–14) agonist peptide. Incubations were continued for 30 min at 21° C. and the resulting cAMP levels were measured by RIA, as described in Experimental Procedures. The final concentration of antagonist peptide present during the incubation was 10 mM. Shown are data from a single experiment performed in triplicate. A repeat of the same experiment yielded equivalent results.
Figure 7B:
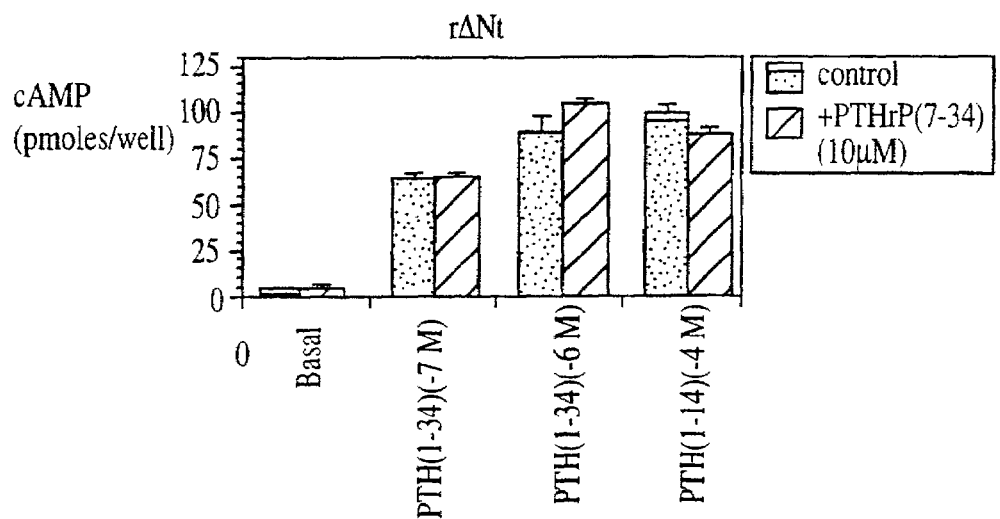

Although there was no direct measurement of receptor expression in this study, the 100-fold reduction in potency that PTH(1–34) exhibited with rΔNt, as compared to rWT-HA, is not likely to be due to a reduction in surface expression of the truncated receptor, since PTH(1–14) exhibited equivalent activity with rΔNt and rWT-HA (FIG. 4, C and D). This suggests that the two receptors are expressed at approximately equal levels. The reduced activity of PTH(1–34) with rΔNt therefore most likely reflects a loss of important binding interactions that normally occur between the (Jüppner, H., et al., *Science* 254:1024–1026 (1991), Guo, J., et al., *Endocrinology* 136:3884–3891 (1995); Hruska, K. A., *J. Clin. Invest.* 79:230–239 (1987); Donahue, H. J., et al., *J. Biol. Chem.* 263:13522–13527 (1988); Kolakowski, L. F., GCRDb: *A G-protein-coupled receptor Database Receptors and Channels* 2:1–7 (1994); Jüppner, H., et al., *Endocrinology* 134:879–884 (1994); Lee, C., et al., *Mol. Endo.* 9:1269–1278 (1995); Turner, P., et al., Single Mutations Allow the PTH-2 Receptor to Respond to PTHrP J. Bone Min. Res. 12, Supplement 1, Abstract #121 (1997); Dautzenberg, F., et al., *Proc. Natl. Acad. Sci.* 95:4941–4946 (1998), Holtmann, M., et al., *J. Biol. Chem.* 270:14394–14398 (1995); DeAlmeida, V., et al., *Mol. Endo.* 12:750–765 (1998); Stroop, S., et al., *Biochem.* 34:1050–1057 (1994); Zhou, A., et al., *Proc. Natl. Acad. Sci. USA* 94:3644–3649 (1997); Bisello, A., et al., *J. Biol. Chem.* 273:22498–22505 (1998); Bergwitz, C., et al., *J. Biol. Chem.* 271:26469–26472 (1996); Gardella, T. J., et al., *Endocrinology* 135:1186–1194 (1994); Mannstadt, M., et al., *J. Biol. Chem.* 273:16890–16896 (1998); Takasu, H. and Bringhurst, F., *Endocrinology*, in press (1998); Bergwitz, C., et al., *J. Biol. Chem.* 272:28861–28868 (1997); Lee, C., et al., *Endocrinology* 135(4):1488–1495 (1994)) domain of the ligand and the amino-terminal domain of the receptor (Jüppner, H., et al., *Endocrinology* 134:879–884 (1994); Bergwitz, C., et al., *J. Biol. Chem.* 271:16469–26472 (1996); Mannstadt, M., et al., *J. Biol. Chem.* 273:16890–16896 (1998)). The lack of these same binding interactions could also explain the inability of PTHrP(7–34) to function as an antagonist with rΔNt (see FIG. 7B).

Example 4

Figure 5A:
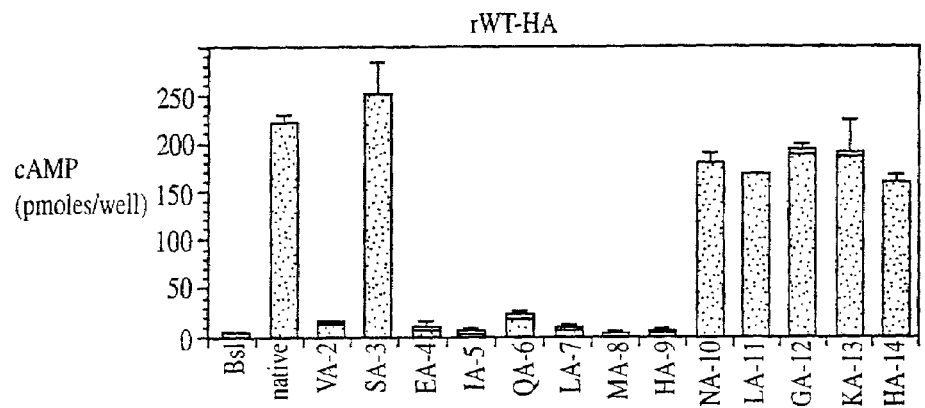
FIG. 5. Alanine-scan of PTH(1–14) with Intact and Truncated PTH Receptors. COS-7 cells transiently transfected with rWT-HA (A) or rCE I-G (B) were treated with 100 mM of native rat PTH(1–14) or 100 mM of a rPTH(1–14) analog containing a single alanine substitution for 1 h at 21° C., and the resulting intracellular cAMP levels were measured by RIA. The amino acid substitutions are indicated on the axis labels. Peptides were tested in duplicate, and a single experiment representative of three others is shown.
Figure 5B:
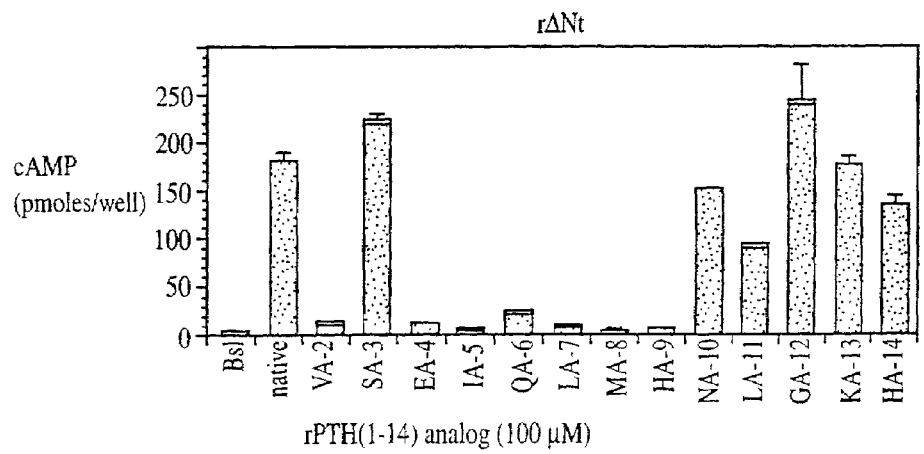

The rΔNt Receptor Interacts with the Same PTH(1–14) Functional Residues as Intact PTH-1 Receptor Experiments were designed to test whether the PTH (1–14) residues that are required for function with the truncated receptor differ from those required for function with the intact receptor. Using the alanine-scanning set of PTH(1–14) analogs, experiments tested cAMP-stimulating activity for the two rat PTH-1 receptors in COS-7 cells. As shown in FIGS. 5A and 5B, the activity profiles obtained with rΔNt mirrored that obtained with rWT-HA, since Ser-3 and the 10–14 region of the peptide were tolerant of mutation, whereas residues 2 and 4–9 were intolerant (FIGS. 4A and B). Therefore, the same set of functional residues in PTH(1–14) that are required for interaction with the intact PTH-1 receptor are also required for interaction with the core domain of the receptor.

Example 5

Specificity of Truncated Ligands and PTH-Receptors

Figure 6A:
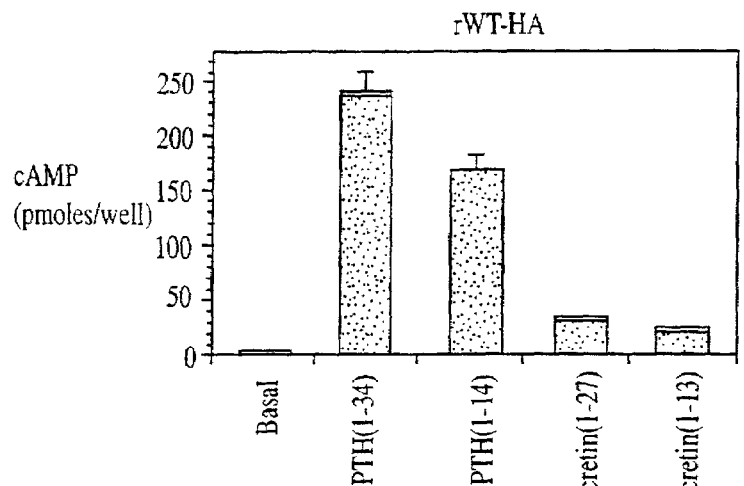
FIG. 6. Specificity of the Truncated Ligand and PTH Receptor. COS-7 cells transiently transfected with either rWT-HA (A), rΔNt (B), or the intact rat secretin receptor (C), were treated with the indicated peptides for 60 min at 22° C., and the resulting intracellular cAMP levels were quantified by RIA. Concentration of peptides present during the incubations were: rPTH(1–34), 0.1 mM; rPTH(1–14) 100 mM; secretin(1–27). 1 mM and secretin(1–13), 100 mM. Shown are data (mean±s.e.m.) from one experiment performed in duplicate, and this was repeated twice more with equivalent results.
Figure 6B:
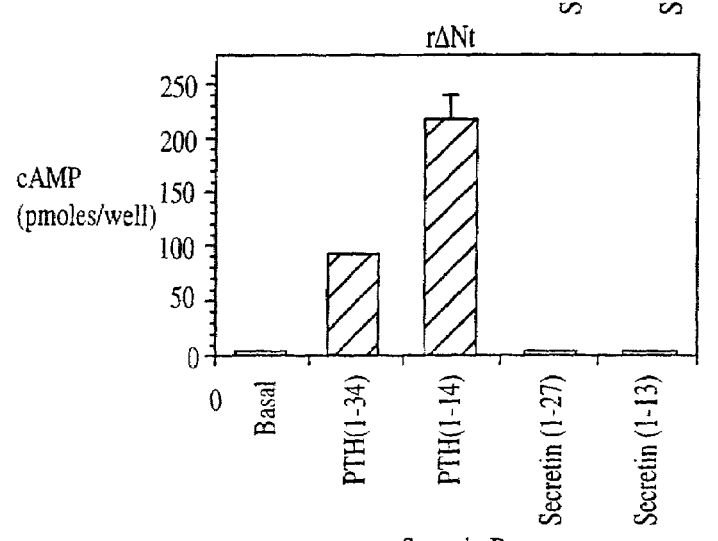
Figure 6C:
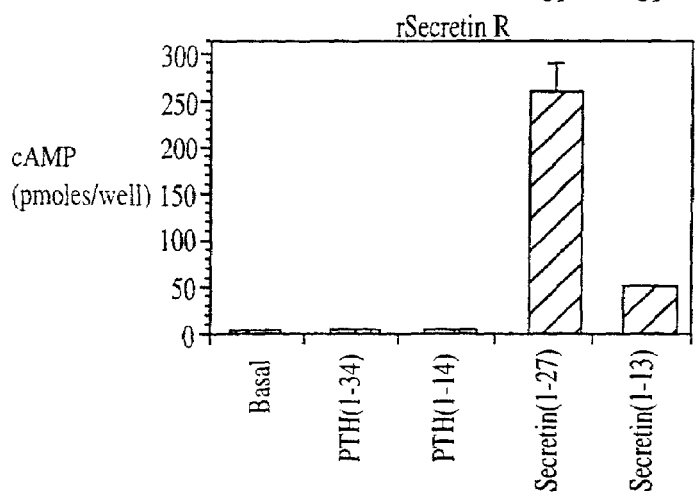

In order to test whether PTH(1–14) and rΔNt retained the appropriate recognition specificity for the corresponding parent ligand, cross-reactivity experiments were done using secretin ligands and the cloned rat secretin receptor. COS-7 cells transfected with the secretin receptor exhibited a 50-fold increase in cAMP levels in response to secretin (1–27) (1 mM), but did not respond to either PTH(1–34) (1 mM) or PTH(1–14) (100 mM) (FIG. 5C). Cells expressing rΔNt responded to PTH(1–34) and PTH(1–14) but not to secretin(1–27) (1 mM) or secretin(1–13) (1 mM) (FIG. 5B). Thus, the recognition specificity of PTH(1–14) and rΔNt appear to replicate that of the intact parent molecules. No evidence for relaxed specificity was detected in these studies (FIG. 6). It is also worth noting that PTH(1–14) did not activate the endogenous calcitonin receptors expressed in LLC-PK1 cells (FIG. 2B).

Example 6 rΔNt Stimulation is not Affected by the Inhibitor [Leu11,D-Trp12]hPTHrP(7–34)NH2

In order to determine whether [Leu11,D-Trp12]hPTHrP (7–34)NH2, a potent competitive antagonist of PTH(1–34) action (Nutt, R. F., et al., *Endocrinology* 127:491–493 (1990)), could block the ability of PTH(1–14) to stimulate cAMP formation in COS-7 cells expressing either rWT-HA or rΔNt (FIG. 6). With rWT-HA the inhibitor peptide reduced the efficacy of both PTH(1–14) and PTH(1–34) by as much as 70% as compared to the responses elicited by these agonists in the absence of inhibitor (FIG. 6A). In contrast, PTHrP(7–34) had little or no effect on the ability of PTH(1–34) or PTH(1–14) to stimulate cAMP production in cells expressing rΔNt.

The ability of PTHrP(7–34) to antagonize PTH(1–14) action on the intact receptor (FIG. 6A) suggests that the receptor sites occupied by these two ligands overlap. This overlap could involve ligand residues 7–14 and some portion in the core region of the receptor. Any binding interactions that may occur between figure residues (7–34) and the core region of the receptor are, however, too weak to enable effective antagonism in the absence of the amino-terminal extracellular receptor domain.

These findings establish that a much smaller region of PTH(1–34) than heretofore appreciated can stimulate receptor activation, and that the amino-terminal portion of PTH the hormone interacts with the core region of the receptor containing the seven transmembrane helices and connecting loops, as previously hypothesized for intact PTH ligands and receptors (Lee, C., et al., *Mol. Endo.* 9:1269–1278 (1995); Bisello, A., et al., *J. Biol. Chem.* 273:22498–22505 (1998); Bergwitz, C., et al., *J. Biol. Chem.* 271:26469–26472 (1996); Gardella, T. J., et al., *Endocrinology* 135:1186–1194 (1994); Bergwitz, C., et al., *J. Biol. Chem.* 272:28861–28868; Gardella, T., et al., *J. Biol. Chem.* 271: 12820–12825 (1996)). Furthermore, this component of the interaction is sufficient for receptor signaling. The hypothesis that the 15–34 region of PTH binds to the amino-terminal extracellular domain of the receptor does not exclude the possibility that this domain, which by itself does not stimulate cAMP formation (data not shown), also provides some binding energy by interacting with the core region of the receptor. In fact, the 100-fold greater potency that PTH(1–34) exhibits with rΔNt, in comparison to the potency of PTH(1–14) with this receptor (FIG. 4D), might well be due to such interactions. However, we can not exclude the alternative possibility that the 15–34 domain enhances the intrinsic signaling activity of the (1–14) segment, for example, by stabilizing a favorable secondary structure in the amino-terminal portion of the ligand. More specific information on the receptor recognition sites utilized by PTH and the structure of the receptor-bound ligand are required to distinguish between such possibilities.

Some recognition determinants have been identified in the amino-terminal extracellular domain, the extracellular loops and the transmembrane helices of the B family of receptors (Turner, P., et al., Single Mutations Allow the PTH-2 Receptor to Respond to PTHrP J. Bone Min. Res. 12, Supplement 1, Abstract #121 (1997), Dautzenberg, F., et al., *Proc. Natl. Acad. Sci.* 95:4941–4946 (1998), Holtmann, M., et al., *J. Biol. Chem.* 270:14394–14398 (1995), Gardella, T. J., et al., *Endocrinology* 135:1186–1194 (1994); Bergwitz, C., et al., *J. Biol. Chem.* 272:28861–28868; Turner, P. R., et al., *J. Biol. Chem.* 271(16):9205–9208 (1996)).

One distinguishing feature of the family B receptors is the amino-terminal extracellular domain, which is relatively large and contains a number of conserved residues, including six cysteines. It is thus intriguing that this domain of the PTH-1 receptor is not essential for ligand-dependent signal transduction, as evidenced by the results with the rΔNt receptor.

Several other reports on other family B receptors provide additional evidence to suggest that the amino-terminal extracellular domains of these receptors may not be essential for functional expression. Large amino-terminal deletions in the calcitonin receptor (Unson, C., et al., *J. Biol. Chem.* 270: 27720–27727 (1995)) and in the growth hormone-releasing factor receptor (DeAlmedia, V. and Mayo, K., *Mol. Endo.* 12:750–765 (1998)) were compatible with expression, as assessed by immunologic methods, and a glucagon receptor lacking the amino-terminal domain and containing an activating mutation in helix 2 (HR-178) exhibited constitutive cAMP-signaling activity (Hjorth, S., et al., *Mol. Endo.* 12:78–86 (1998)). In these studies, however, evidence that the truncated receptor could interact with ligand. as we have found for the PTH-1 receptor, was not reported. In a separate study on the lutropin receptor, a group A receptor that binds the large glycohormone human choriogonadotropin, it was observed that a deletion of the large amino-terminal extracellular domain yielded a receptor that could mediate a cAMP response to high doses of hCG (Ji, I. H. and Ji, T. H., *J. Biol. Chem.* 266(20):13076–13079 (1991)).

That the activity of PTH(1–14) was not affected by the deletion of the amino-terminal receptor domain suggests that the peptide interacts predominantly with the core region of the receptor. This conclusion is supported by the alanine-scanning experiments performed on PTH(1–14), in which the profile of tolerant and intolerant residues observed with rΔNt was nearly the same as that obtained with the intact receptor (FIG. 4). With each receptor, residues in the 10–14 region of the ligand formed a tolerant segment, while residues in the 1–9 region, excluding 1 and 3, formed an intolerant segment. This pattern of critical and non-critical residues observed in the context of the PTH(1–14) fragment closely matches the patterns found previously in studies on longer-length PTH analogs (Cohen, F. E., et al., *J. Biol. Chem.* 266:1997–2004 (1991); Gombert, F., et al., in "Peptides: Chemistry, Structure and Biology Proceedings of the 14th American Peptide Symposium June 18–23, Kaumaya, P. and Hodges, R., eds., pp. 661–662, *Mayflower Scientific Limited*, Kingswinford, UK (1996); Gardella, T. J., et al., *J. Biol. Chem.* 266:13141–13146 (1991)).

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A method of screening for an agonist or an antagonist of PTH receptor activity comprising:
 (a) contacting cells with a test compound wherein said cells express a rΔNt polypeptide, wherein said cells comprise a polynucleotide having a nucleotide sequence selected from the group consisting of:
  (i) a nucleotide sequence from position 1 to position 1320 in SEQ ID NO:1;
  (ii) a nucleotide sequence from position 4 to position 1320 in SEQ ID NO:1;
  (iii) a nucleotide sequence from position 67 to position 1320 in SEQ ID NO:1;
  (iv) a nucleotide sequence encoding the rΔNt polypeptide having the amino acid sequence encoded by the cDNA clone contained in ATCC Deposit No. PTA-1136; and
  (v) a nucleotide sequence encoding the mature rΔNt polypeptide having the amino acid sequence encoded by the cDNA clone contained in ATCC Deposit No. PTA-1136;
 wherein said polypeptide comprises a deletion of the extracellular amino-terminal ligand binding domain of a PTH-1 receptor and
 wherein said polypeptide increases intracellular cAMP levels when activated by PTH or PTH-related peptide and wherein said extracellular amino-terminal ligand binding domain has an amino acid sequence from residue 26 to residue 181 in wild-type PTH receptor;
 (b) measuring cAMP accumulation in said cells; and
 (c) determining whether said test compound is an agonist or an antagonist of PTH receptor activity;
wherein an agonist is identified as a compound that increases cAMP accumulation and an antagonist prevents cAMP accumulation.

2. The method of claim 1, wherein said cells comprise a polynucleotide having a nucleotide sequence from position 1 to position 1320 in SEQ ID NO:1.

3. A method of screening for an agonist or an antagonist of PTH receptor activity comprising:
 (a) contacting cells with a test compound wherein said cells express a rΔNt polypeptide having an amino acid sequence selected from the group consisting of:
  (i) the amino acid sequence from position 1 to position 435 in SEQ ID NO:2;
  (ii) the amino acid sequence from position 2 to position 435 in SEQ ID NO:2;
  (iii) the amino acid sequence from position 23 to position 435 in SEQ ID NO:2;
  (iv) the amino acid sequence of the rΔNt polypeptide having the amino acid sequence encoded by the cDNA clone contained in ATCC Deposit No. PTA-1136; and
  (v) the amino acid sequence of the mature rΔNt polypeptide having the amino acid sequence encoded by the cDNA clone contained in ATCC Deposit No. PTA-1136;
 wherein said polypeptide comprises a deletion of the extracellular amino-terminal ligand binding domain of a PTH-1 receptor, said extracellular amino-terminal ligand binding domain having an amino acid sequence from residue 26 to residue 181 in wild-type PTH receptor;
 (b) measuring cAMP accumulation in said cells; and
 (c) determining whether said test compound is an agonist or an antagonist of PTH receptor activity;
wherein an agonist is identified as a compound that increases cAMP accumulation and an antagonist prevents cAMP accumulation.

4. The method of claim 3, wherein said cells express a rΔNt polypeptide having an amino acid sequence from position 1 to position 435 in SEQ ID NO:2.

5. A method of screening for an agonist or an antagonist of PTH receptor activity comprising:
 (a) contacting cells with a test compound wherein said cells express a rΔNt polypeptide, wherein said cells comprise a polynucleotide having a nucleotide sequence selected from the group consisting of:
  (i) a nucleotide sequence encoding the amino acid sequence from position 1 to position 435 in SEQ ID NO:2;
  (ii) a nucleotide sequence encoding the amino acid sequence from position 2 to position 435 in SEQ ID NO:2;
  (iii) a nucleotide sequence encoding the amino acid sequence from position 23 to position 435 in SEQ ID NO:2;
  (iv) a nucleotide sequence encoding the rΔNt polypeptide having the amino acid sequence encoded by the cDNA clone contained in ATCC Deposit No. PTA-1136; and
  (v) a nucleotide sequence encoding of the mature rΔNt polypeptide having the amino acid sequence encoded by the cDNA clone contained in ATCC Deposit No. PTA-1136;
 wherein said polypeptide comprises a deletion of the extracellular amino-terminal ligand binding domain of a PTH-1 receptor, said extracellular amino-terminal ligand binding domain having an amino acid sequence from residue 26 to residue 181 in wild-type PTH receptor;
 (b) measuring the biological response of cAMP accumulation in said cells; and
 (c) determining whether said test compound is an agonist or an antagonist of PTH receptor activity;

wherein an agonist is identified as a compound that increases cAMP accumulation and an antagonist prevents cAMP accumulation.

6. The method of claim 5, wherein said cells comprise a polynucleotide which encodes a polypeptide having the amino acid sequence from 1 to position 435 in SEQ ID NO:2.

7. A method of screening for an agonist or an antagonist of PTH receptor activity comprising:
（a) providing an iodinated test compound;
(b) contacting cells with said iodinated test compound wherein said cells express a rΔNt polypeptide, wherein said cells comprise a polynucleotide having a nucleotide sequence selected from the group consisting of:
(i) a nucleotide sequence from position 1 to position 1320 in SEQ ID NO:1;
(ii) a nucleotide sequence from position 4 to position 1320 in SEQ ID NO:1;
(iii) a nucleotide sequence from position 67 to position 1320 in SEQ ID NO:1;
(iv) a nucleotide sequence encoding the rΔNt polypeptide having the amino acid sequence encoded by the cDNA clone contained in ATCC Deposit No. PTA-1136; and
(v) a nucleotide sequence encoding the mature rΔNt polypeptide having the amino acid sequence encoded by the cDNA clone contained in ATCC Deposit No. PTA-1136;
wherein said polypeptide comprises a deletion of the extracellular amino-terminal ligand binding domain of a PTH-1 receptor and
wherein said polypeptide increases intracellular cAMP levels when activated by PTH or PTH-related peptide and wherein said extracellular amino-terminal ligand binding domain has an amino acid sequence from residue 26 to residue 181 in wild-type PTH receptor; and
(c) measuring cAMP accumulation in said cells; and
(d) determining whether said iodinated test compound competitively binds to said rΔNt polypeptide;
wherein an agonist is identified as a compound that increases cAMP accumulation and an antagonist prevents cAMP accumulation.

8. The method of claim 7, wherein said cells comprise a polynucleotide having a nucleotide sequence from position 1 to position 1320 in SEQ ID NO:1.

9. A method of screening for an agonist or an antagonist of PTH receptor activity comprising:
(a) providing an iodinated test compound;
(b) contacting cells with said iodinated test compound wherein said cells express a rΔNt polypeptide having an amino acid sequence selected from the group consisting of:
(i) the amino acid sequence from position 1 to position 435 in SEQ ID NO:2;
(ii) the amino acid sequence from position 2 to position 435 in SEQ ID NO:2;
(iii) the amino acid sequence from position 23 to position 435 in SEQ ID NO:2;
(iv) the amino acid sequence of the rΔNt polypeptide having the amino acid sequence encoded by the cDNA clone contained in ATCC Deposit No. PTA-1136; and
(v) the amino acid sequence of the mature rΔNt polypeptide having the amino acid sequence encoded by the cDNA clone contained in ATCC Deposit No. PTA-1136;
wherein said polypeptide comprises a deletion of the extracellular amino-terminal ligand binding domain of a PTH-1 receptor and
wherein said polypeptide increases intracellular cAMP levels when activated by PTH or PTH-related peptide and wherein said extracellular amino-terminal ligand binding domain has an amino acid sequence from residue 26 to residue 181 in wild-type PTH receptor; and
(c) measuring cAMP accumulation in said cells; and
(d) determining whether said iodinated test compound competitively binds to said rΔNt polypeptide;
wherein an agonist is identified as a compound that increases cAMP accumulation and an antagonist prevents cAMP accumulation.

10. The method of claim 9 wherein said cells express a rΔNt polypeptide having an amino acid sequence from position 1 to position 435 in SEQ ID NO:2.

* * * * *

UNITED STATES PATENT AND TRADEMARK OFFICE
CERTIFICATE OF CORRECTION

| | | |
|---|---|---|
| PATENT NO. | : 7,169,567 B1 | Page 1 of 4 |
| APPLICATION NO. | : 09/869565 | |
| DATED | : January 30, 2007 | |
| INVENTOR(S) | : Gardella et al. | |

It is certified that error appears in the above-identified patent and that said Letters Patent is hereby corrected as shown below:

On the Title Page, Item (75) under Inventors, replace "Thomas J. Gardella, Needham, MA" with --Thomas J. Gardella, Boston, MA--;

Item (56) under OTHER PUBLICATIONS, in Abou-Samra et al., replace "Parathyroid Hormoe Receptors" with --Parathyroid Hormone Receptors--.

Title Page 2, Item (56) under OTHER PUBLICATIONS, in Abou-Samra et al., replace "Relateed" with --Related--;

Item (56) under OTHER PUBLICATIONS, in Abou-Samra et al., replace "Peptied" with --Peptide--;

Item (56) under OTHER PUBLICATIONS, in Abou-Samra et al., replace "Recceptor" with --Receptor--;

Item (56) under OTHER PUBLICATIONS, in Barbier et al., replace "Americna Chemical Society" with --American Chemical Society--;

Item (56) under OTHER PUBLICATIONS, in Bennett et al., replace "Development of a ELISA" with --Development of an ELISA--;

Item (56) under OTHER PUBLICATIONS, in Bergwitz et al., replace "Signaling Selecivity" with --Signaling Selectivity--;

Item (56) under OTHER PUBLICATIONS, in Bowie et al., replace "Protein Seuences:" with --Protein Sequences:--;

Signed and Sealed this
Seventh Day of February, 2012

David J. Kappos
*Director of the United States Patent and Trademark Office*

CERTIFICATE OF CORRECTION (continued)
U.S. Pat. No. 7,169,567 B1

Title Page 2, Item (56) under OTHER PUBLICATIONS, in Chorev et al., replace "Thyroid the Design" with --Toward the Design--;

Item (56) under OTHER PUBLICATIONS, in Gentz et al., replace "Trans-activated" with --Trans-activation--;

Item (56) under OTHER PUBLICATIONS, in Horiuchi et al., replace "American Association for the Adancement of Science" with --American Association for the Advancement of Science--;

Item (56) under OTHER PUBLICATIONS, in Jüppner et al., replace "The Extraceullular Animo-Terminal Region" with --The Extracellular Amino-Terminal Region--.

Title Page 3, Item (56) under OTHER PUBLICATIONS, in Lee et al., replace "Role of the Extacellular Regions" with --Role of the Extracellular Regions--;

Item (56) under OTHER PUBLICATIONS, in Stroop et al., replace "*Science 237:983-896*" with --*Science 237:893-896*--.

Title Page 4, Item (56) under OTHER PUBLICATIONS, in Bettoun et al., replace "Development Upregulation" with --Developmental Upregulation--;

Item (56) under OTHER PUBLICATIONS, in Potts et al., replace "3$_{rd}$ Edition" with --3$^{rd}$ Edition--;

Title Page 4, Item (56) under OTHER PUBLICATIONS, in Schipani et al., replace "Indentical Complementary Deoxyribonucleic Acids" with --Identical Complementary Deoxyribonucleic Acids--;

Item (56) under OTHER PUBLICATIONS, in Sutcliffe et al., replace "Proteins,"*Science*" with --Proteins," *Science*--.

Column 1, Line 49, replace "*Pathobilogy Annual*" with --*Pathobiology Annual*--.

Column 2, Lines 53-54, replace "*Pathobilogy Annual*" with --*Pathobiology Annual*--.

Column 3, Line 1, replace "need in the art develop" with --need in the art to develop--.

CERTIFICATE OF CORRECTION (continued)
U.S. Pat. No. 7,169,567 B1

Column 4, Line 18, replace "for 5 min at 22EC" with --for 5 min at 22°C--.

Column 5, Line 19, replace "rat PTH 1 receptor." with --rat PTH-1 receptor.--;

Line 30, replace "species on the protein." with --species of the protein.--.

Column 7, Line 20, replace "at fragments least about" with --fragments at least about--.

Column 10, Line 5 replace "Wis. 53711. Bestfit" with --Wis. 53711). Bestfit--.

Column 11, Line 2, replace "significantly effect" with --significantly affect--.

Column 14, Lines 46-47, replace "the deposited the cDNA" with --the deposited cDNA--.

Column 15, Line 51, replace "is used a tracer" with --is used as a tracer--;

Line 53, replace "C18 SEP-PAK cartridge" with --SEP-PAK C18 cartridge--;

Lines 56-58, replace "(TFA). The iodinated cAMP analog is lyophilized, reconstituted in 1 ml 0.1% TFA, and injected" with --(TFA), and injected--.

Column 16, Lines 8-9, replace "polyethyleneglycol" with --polyethylene glycol--;

Line 34, replace "heat-inactived horse serum" with --heat-inactivated horse serum--;

Lines 42-43, replace "utilized in to screen" with --utilized to screen--.

Column 17, Line 40, replace "MALDI-mass spectromety" with --MALDI-mass spectrometry--.

CERTIFICATE OF CORRECTION (continued)
U.S. Pat. No. 7,169,567 B1

Column 18, Line 8, replace "encodin" with --encoding--;

Line 19, replace "residues Dautzenberg," with --residues (Dautzenberg,--;

Line 34, replace "2 mM CaCl2" with --2 mM CaCl$_2$--.

Column 19, Line 5, replace "PH(1-13) and shorter fragments" with --PH(1-13), and for shorter--;

Line 23, replace "*Endrocrinology*" with --*Endocrinology*--;

Line 61, replace "Potentcy" with --Potency--.

Column 20, Line 34, replace "PTHrP J. Bone Min. Res." with --PTHrP, *J. Bone Min. Res.*--.

Column 21, Line 35, replace "[Leu11,D-Trp12]hPTHrP(7-34)NH2" with --[Leu11,D-Trp12]hPTHrP(7-34)NH$_2$--;

Lines 60-61, replace "the amino-terminal portion of PTH the hormone" with --the amino-terminal portion of the PTH hormone--.

Column 22, Line 10, replace "the 100-fold" with --the ~100-fold--;

Column 22, Line 13, replace "can not" with --cannot--;

Line 25, replace "PTHrP J. Bone Min. Res." with --PTHrP, *J. Bone Min. Res.*--;

Line 29, replace "*Endrocrinology*" with --*Endocrinology*--;

Line 52, replace "with ligand. as we have" with --with ligand, as we have--.

Column 23, Lines 7-8, replace ""Peptides: Chemistry, Structure and Biology" with --"Peptides: Chemistry, Structure and Biology"--.

SEQUENCE LISTING

```
<160> NUMBER OF SEQ ID NOS: 2

<210> SEQ ID NO 1
<211> LENGTH: 1320
<212> TYPE: DNA
<213> ORGANISM: Artificial Sequence
<220> FEATURE:
<223> OTHER INFORMATION: Description of Artificial Sequence: cDNA
<221> NAME/KEY: CDS
<222> LOCATION: (1)..(1308)

<400> SEQUENCE: 1 atg ggg gcc gcc cgg atc gca ccc agc ctg gcg ctc cta ctc tgc tgc        48
Met Gly Ala Ala Arg Ile Ala Pro Ser Leu Ala Leu Leu Leu Cys Cys
 1               5                  10                  15 cca gtg ctc agc tcc gca tat gcg ctg gag gta ttt gac cgc cta ggc        96
Pro Val Leu Ser Ser Ala Tyr Ala Leu Glu Val Phe Asp Arg Leu Gly
             20                  25                  30 atg atc tac acc gtg gga tac tcc atg tct ctc gcc tcc ctc acg gtg       144
Met Ile Tyr Thr Val Gly Tyr Ser Met Ser Leu Ala Ser Leu Thr Val
         35                  40                  45 gct gtg ctc atc ctg gcc tat ttt agg cgg ctg cac tgc acg cgc aac       192
Ala Val Leu Ile Leu Ala Tyr Phe Arg Arg Leu His Cys Thr Arg Asn
     50                  55                  60 tac atc cac atg cac atg ttc ctg tcg ttt atg ctg cgc gcc gcg agc       240
Tyr Ile His Met His Met Phe Leu Ser Phe Met Leu Arg Ala Ala Ser
 65                  70                  75                  80 atc ttc gtg aag gac gct gtg ctc tac tct ggc ttc acg ctg gat gag       288
Ile Phe Val Lys Asp Ala Val Leu Tyr Ser Gly Phe Thr Leu Asp Glu
                 85                  90                  95 gcc gag cgc ctc aca gag gaa gag ttg cac atc atc gcg cag gtg cca       336
Ala Glu Arg Leu Thr Glu Glu Glu Leu His Ile Ile Ala Gln Val Pro
            100                 105                 110 cct ccg ccg gcc gct gcc gcc gta ggc tac gct ggc tgc cgc gtg gcg       384
Pro Pro Pro Ala Ala Ala Ala Val Gly Tyr Ala Gly Cys Arg Val Ala
        115                 120                 125 gtg acc ttc ttc ctc tac ttc ctg gct acc aac tac tac tgg atc ctg       432
Val Thr Phe Phe Leu Tyr Phe Leu Ala Thr Asn Tyr Tyr Trp Ile Leu
    130                 135                 140 gtg gag ggg ctg tac ttg cac agc ctc atc ttc atg gcc ttt ttc tca       480
Val Glu Gly Leu Tyr Leu His Ser Leu Ile Phe Met Ala Phe Phe Ser
145                 150                 155                 160 gag aag aag tac ctg tgg ggc ttc acc atc ttt ggc tgg ggt cta ccg       528
Glu Lys Lys Tyr Leu Trp Gly Phe Thr Ile Phe Gly Trp Gly Leu Pro
                165                 170                 175 gct gtc ttc gtg gct gtg tgg gtc ggt gtc aga gca acc ttg gcc aac       576
Ala Val Phe Val Ala Val Trp Val Gly Val Arg Ala Thr Leu Ala Asn
            180                 185                 190 act ggg tgc tgg gat ctg agc tcc ggg cac aag aag tgg atc atc cag       624
```

```
                Thr Gly Cys Trp Asp Leu Ser Ser Gly His Lys Lys Trp Ile Ile Gln
                        195                 200                 205 gtg ccc atc ctg gca tct gtt gtg ctc aac ttc atc ctt ttt atc aac        672
Val Pro Ile Leu Ala Ser Val Val Leu Asn Phe Ile Leu Phe Ile Asn
210                 215                 220 atc atc cgg gtg ctt gcc act aag ctt cgg gag acc aat gcg ggc cgg        720
Ile Ile Arg Val Leu Ala Thr Lys Leu Arg Glu Thr Asn Ala Gly Arg
225                 230                 235                 240 tgt gac acc agg cag cag tac cgg aag ctg ctc agg tcc acg ttg gtg        768
Cys Asp Thr Arg Gln Gln Tyr Arg Lys Leu Leu Arg Ser Thr Leu Val
                245                 250                 255 ctc gtg ccg ctc ttt ggt gtg cac tac acc gtc ttc atg gcc ttg ccg        816
Leu Val Pro Leu Phe Gly Val His Tyr Thr Val Phe Met Ala Leu Pro
                260                 265                 270 tac acc gag gtc tca ggg aca ttg tgg cag atc cag atg cat tat gag        864
Tyr Thr Glu Val Ser Gly Thr Leu Trp Gln Ile Gln Met His Tyr Glu
                275                 280                 285 atg ctc ttc aac tcc ttc cag gga ttt ttt gtt gcc atc ata tac tgt        912
Met Leu Phe Asn Ser Phe Gln Gly Phe Phe Val Ala Ile Ile Tyr Cys
        290                 295                 300 ttc tgc aat ggt gag gtg cag gca gag att agg aag tca tgg agc cgc        960
Phe Cys Asn Gly Glu Val Gln Ala Glu Ile Arg Lys Ser Trp Ser Arg
305                 310                 315                 320 tgg aca ctg gcg ttg gac ttc aag cgc aaa gca cga agt ggg agt agc       1008
Trp Thr Leu Ala Leu Asp Phe Lys Arg Lys Ala Arg Ser Gly Ser Ser
                325                 330                 335 agc tac agc tat ggc cca atg gtg tct cac acg agt gtg acc aat gtg       1056
Ser Tyr Ser Tyr Gly Pro Met Val Ser His Thr Ser Val Thr Asn Val
                340                 345                 350 ggc ccc cgt gca gga ctc agc ctc ccc ctc agc ccc cgc ctg cct cct       1104
Gly Pro Arg Ala Gly Leu Ser Leu Pro Leu Ser Pro Arg Leu Pro Pro
                355                 360                 365 gcc act acc aat ggc cac tcc cag ctg cct ggc cat gcc aag cca ggg       1152
Ala Thr Thr Asn Gly His Ser Gln Leu Pro Gly His Ala Lys Pro Gly
370                 375                 380 gct cca gcc act gag act gaa acc cta cca gtc act atg gcg gtt ccc       1200
Ala Pro Ala Thr Glu Thr Glu Thr Leu Pro Val Thr Met Ala Val Pro
385                 390                 395                 400 aag gac gat gga ttc ctt aac ggc tcc tgc tca ggc ctg gat gag gag       1248
Lys Asp Asp Gly Phe Leu Asn Gly Ser Cys Ser Gly Leu Asp Glu Glu
                405                 410                 415 gcc tcc ggg tct gcg cgg ccg cct cca ttg ttg cag gaa gga tgg gaa       1296
Ala Ser Gly Ser Ala Arg Pro Pro Pro Leu Leu Gln Glu Gly Trp Glu
                420                 425                 430 aca gtc atg tga ctgggcacta gg                                         1320
Thr Val Met
        435

<210> SEQ ID NO 2
<211> LENGTH: 435
<212> TYPE: PRT
<213> ORGANISM: Artificial Sequence
<220> FEATURE:
<223> OTHER INFORMATION: Description of Artificial Sequence: rat protein
      sequence that has been mutated in the laboratory, creating a
      deletion in the original sequence.

<400> SEQUENCE: 2

Met Gly Ala Ala Arg Ile Ala Pro Ser Leu Ala Leu Leu Leu Cys Cys
 1               5                  10                  15

Pro Val Leu Ser Ser Ala Tyr Ala Leu Glu Val Phe Asp Arg Leu Gly
```

-continued

```
                    20                  25                  30
Met Ile Tyr Thr Val Gly Tyr Ser Met Ser Leu Ala Ser Leu Thr Val
                35                  40                  45
Ala Val Leu Ile Leu Ala Tyr Phe Arg Arg Leu His Cys Thr Arg Asn
 50                  55                  60
Tyr Ile His Met His Met Phe Leu Ser Phe Met Leu Arg Ala Ala Ser
 65                  70                  75                  80
Ile Phe Val Lys Asp Ala Val Leu Tyr Ser Gly Phe Thr Leu Asp Glu
                85                  90                  95
Ala Glu Arg Leu Thr Glu Glu Leu His Ile Ile Ala Gln Val Pro
                100                 105                 110
Pro Pro Pro Ala Ala Ala Val Gly Tyr Ala Gly Cys Arg Val Ala
                115                 120                 125
Val Thr Phe Phe Leu Tyr Phe Leu Ala Thr Asn Tyr Tyr Trp Ile Leu
                130                 135                 140
Val Glu Gly Leu Tyr Leu His Ser Leu Ile Phe Met Ala Phe Phe Ser
145                 150                 155                 160
Glu Lys Lys Tyr Leu Trp Gly Phe Thr Ile Phe Gly Trp Gly Leu Pro
                165                 170                 175
Ala Val Phe Val Ala Val Trp Val Gly Val Arg Ala Thr Leu Ala Asn
                180                 185                 190
Thr Gly Cys Trp Asp Leu Ser Ser Gly His Lys Lys Trp Ile Ile Gln
                195                 200                 205
Val Pro Ile Leu Ala Ser Val Val Leu Asn Phe Ile Leu Phe Ile Asn
                210                 215                 220
Ile Ile Arg Val Leu Ala Thr Lys Leu Arg Glu Thr Asn Ala Gly Arg
225                 230                 235                 240
Cys Asp Thr Arg Gln Gln Tyr Arg Lys Leu Leu Arg Ser Thr Leu Val
                245                 250                 255
Leu Val Pro Leu Phe Gly Val His Tyr Thr Val Phe Met Ala Leu Pro
                260                 265                 270
Tyr Thr Glu Val Ser Gly Thr Leu Trp Gln Ile Gln Met His Tyr Glu
                275                 280                 285
Met Leu Phe Asn Ser Phe Gln Gly Phe Phe Val Ala Ile Ile Tyr Cys
                290                 295                 300
Phe Cys Asn Gly Glu Val Gln Ala Glu Ile Arg Lys Ser Trp Ser Arg
305                 310                 315                 320
Trp Thr Leu Ala Leu Asp Phe Lys Arg Lys Ala Arg Ser Gly Ser Ser
                325                 330                 335
Ser Tyr Ser Tyr Gly Pro Met Val Ser His Thr Ser Val Thr Asn Val
                340                 345                 350
Gly Pro Arg Ala Gly Leu Ser Leu Pro Leu Ser Pro Arg Leu Pro Pro
                355                 360                 365
Ala Thr Thr Asn Gly His Ser Gln Leu Pro Gly His Ala Lys Pro Gly
                370                 375                 380
Ala Pro Ala Thr Glu Thr Glu Thr Leu Pro Val Thr Met Ala Val Pro
385                 390                 395                 400
```

```
Lys Asp Asp Gly Phe Leu Asn Gly Ser Cys Ser Gly Leu Asp Glu Glu
                405                 410                 415

Ala Ser Gly Ser Ala Arg Pro Pro Pro Leu Leu Gln Glu Gly Trp Glu
                420                 425                 430

Thr Val Met
        435
```